United States Patent
Motkuri et al.

(10) Patent No.: US 10,695,741 B2
(45) Date of Patent: Jun. 30, 2020

(54) SYSTEM AND PROCESS FOR CONTINUOUS AND CONTROLLED PRODUCTION OF METAL-ORGANIC FRAMEWORKS AND METAL-ORGANIC FRAMEWORK COMPOSITES

(71) Applicant: BATTELLE MEMORIAL INSTITUTE, Richland, WA (US)

(72) Inventors: Radha Kishan Motkuri, Richland, WA (US); Jagannadha R. Bontha, Richland, WA (US); B. Peter McGrail, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/186,004

(22) Filed: Jun. 17, 2016

(65) Prior Publication Data

US 2017/0361300 A1 Dec. 21, 2017

(51) Int. Cl.

| | | |
|---|---|---|
| *B01J 19/10* | (2006.01) | |
| *B01J 19/06* | (2006.01) | |
| *B01J 19/00* | (2006.01) | |
| *B01J 20/22* | (2006.01) | |
| *B01J 20/30* | (2006.01) | |
| *B01J 31/16* | (2006.01) | |
| *B01J 35/02* | (2006.01) | |
| *B01J 37/00* | (2006.01) | |
| *C07F 15/06* | (2006.01) | |
| *C07F 3/00* | (2006.01) | |
| *C07C 63/307* | (2006.01) | |
| *C07F 15/04* | (2006.01) | |
| *C07C 65/05* | (2006.01) | |
| *C07C 51/43* | (2006.01) | |
| *C07C 51/41* | (2006.01) | |
| *B01J 20/32* | (2006.01) | |
| *C07F 7/00* | (2006.01) | |

(52) U.S. Cl.
CPC .......... *B01J 19/10* (2013.01); *B01J 19/0013* (2013.01); *B01J 19/06* (2013.01); *B01J 20/226* (2013.01); *B01J 20/3085* (2013.01); *B01J 20/3204* (2013.01); *B01J 20/3236* (2013.01); *B01J 20/3293* (2013.01); *B01J 31/1691* (2013.01); *B01J 35/026* (2013.01); *B01J 37/0072* (2013.01); *C07C 51/418* (2013.01); *C07C 51/43* (2013.01); *C07C 63/307* (2013.01); *C07C 65/05* (2013.01); *C07F 3/003* (2013.01); *C07F 7/003* (2013.01); *C07F 15/045* (2013.01); *C07F 15/065* (2013.01); *B01J 2219/00051* (2013.01); *B01J 2219/0877* (2013.01); *B01J 2231/005* (2013.01); *B01J 2531/16* (2013.01); *B01J 2531/845* (2013.01); *B01J 2531/847* (2013.01)

(58) Field of Classification Search
CPC ........................................................ B01J 19/08
See application file for complete search history.

(56) References Cited

U.S. PATENT DOCUMENTS

| | | | | |
|---|---|---|---|---|
| 2,500,056 | A * | 3/1950 | Barr ................... | B01D 11/0269 134/10 |
| 3,735,792 | A * | 5/1973 | Asizawa ................. | B01D 1/18 159/4.04 |
| 5,269,980 | A * | 12/1993 | Levendis ................... | B01J 2/04 264/13 |
| 2007/0264187 | A1 * | 11/2007 | Harutyunyan ........... | B01J 8/002 423/447.3 |
| 2012/0082864 | A1 * | 4/2012 | Leung ..................... | C07F 5/069 428/689 |
| 2015/0231622 | A1 * | 8/2015 | Kitagawa ................. | B01J 21/18 502/152 |

FOREIGN PATENT DOCUMENTS

| | | |
|---|---|---|
| AU | 2015293627 B1 | 12/2015 |
| WO | WO PCT/US2017/026242 | 7/2017 |
| WO | WO PCT/US2017/026242 | 12/2018 |

OTHER PUBLICATIONS

Boissiere et al, Adv. Mater., 2011, 23, 599-623.*
Qi-Long Zhu et al, Metal-organic frameworks, Chem Soc Rev, 43, No. 16, 2014, 5403-6176.*
Albuquerque, G. H., et al., Gas-liquid segmented flow microwave-assisted synthesis of MOF-74(Ni) under moderate pressures, CrystEngComm, 2015-17, 5502-5510.
Batten, M. P., et al., Continuous flow production of metal-organic frameworks, Current Opinion in Chemical Engineering, 2015, 8, 55-59.
Bayliss, P. A., et al., Synthesis of metal-organic frameworks by continuous flow, Royal Society of Chemistry, 16, 2014, 3796-3802.
Carne-Sanchez, A., et al., A spray-drying strategy for synthesis of nanoscale metal-organic frameworks and their assembly into hollow superstructures, Nature Chemistry, 5, 2013, 203-211.
Faustini, M., et al., Microfluidic Approach toward Continuous and Ultrafast Synthesis of Metal-Organic Framework Cyrstals and Hetero Structures in Confined Microdroplets, J. Am. Chem. Soc., 135, 2013, 14619-14626.

(Continued)

*Primary Examiner* — Irina Krylova
(74) *Attorney, Agent, or Firm* — Wells St. John P.S.

(57) ABSTRACT

A MOF production system and method of making are detailed for continuous and controlled synthesis of MOFs and MOF composites. The system can provide optimized yields of MOFs and MOF composites greater than or equal to 95%.

5 Claims, 22 Drawing Sheets

(56) References Cited

OTHER PUBLICATIONS

Joaristi, A. M., et al., Electrochemical Synthesis of Some Archetypical Zn2+, Cu2+, and Al3+ Metal Organic Frameworks, Cryst Growth Des, 12, 2012, 3489-3498.

Rubio-Martinez, M., et al., Versatile, High Quality and Scalable Continuous Flow Productions of Metal-Organic Frameworks, Scientific Reports, 5, 2014, 1-5.

Tai, S., et al., Facile preparation of UiO-66 nanoparticles with tunable sizes in a continuous flow microreactor and its application in drug delivery, Microporous and Mesoporous Materials, 220, 2016, 148-154.

Bang et al., "Applications of Ultrasound to the Synthesis of Nanostructured Materials", Advanced Materials vol. 22, 2010, United States, pp. 1039-1059.

Marquez et al., "Green Scalable Aerosol Synthesis of Porous Metal-Organic Frameworks", Chemical Communicatons vol. 49, 2013, United Kingdom, pp. 3846-3850.

Zhu et al., "Metal-Organic Framework Composites", Chemical Society Reviews vol. 43, No. 16, Aug. 21, 2014, United Kingdom, pp. 5468-5512.

* cited by examiner

POWDER X-RAY DIFFRACTION ANALYSIS

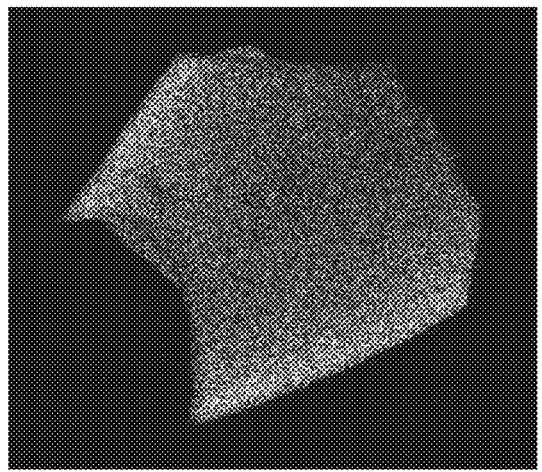
FIG. 11C
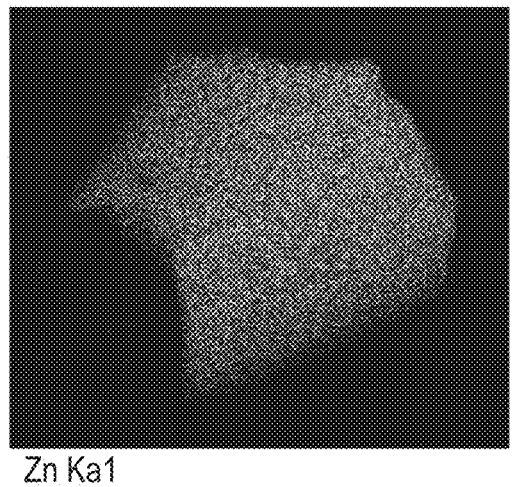
FIG. 11D
| SPECTRUM | Ni | Zn | TOTAL |
|---|---|---|---|
| SUM SPECTRUM | 37.60 | 62.40 | 100 |
EDX
FIG. 11E

SYSTEM AND PROCESS FOR CONTINUOUS AND CONTROLLED PRODUCTION OF METAL-ORGANIC FRAMEWORKS AND METAL-ORGANIC FRAMEWORK COMPOSITES

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

The present invention relates generally to Metal-Organic Frameworks. More particularly, systems and methods for continuous and controlled production of Metal-Organic Frameworks and Metal-Organic Frameworks Composites.

BACKGROUND OF THE INVENTION

Metal-Organic Frameworks (MOFs) have attracted significant attention owing to their structural and chemical diversity. MOFs are compounds with a porous crystalline structure that contain metal ions that cross-link with organic linkers in various coordination networks that form one-, two-, or three-dimensional structures. MOFs have a high surface area, large pore volumes, and various pore dimensions and topologies that make MOFs superior to other porous materials for a variety of applications. MOFs are conventionally synthesized using liquid batch methods in various solvents or aqueous solvents under so-called solvothermal or hydro-thermal conditions. Many MOFs are prepared in pure N,N-diethylformamide (DEF) or N,N-dimethylformamide (DMF) or a combination of solvents that include DMF which decompose at reaction temperatures between 50° C. and 250° C. generating an amine base that deprotonates functionalities of the organic linker to form the selected metal-organic framework (MOF).

However, conventional batch synthesis of MOFs has well-known and significant disadvantages. It is well known, for example, that liquid batch synthesis of MOFs produces partially formed products, unreacted products, and contaminates that cannot be removed from the solvents. Contamination of solvents and liquid precursor materials means solvents cannot be reused and must be replaced after every production run. Solvents alone account for nearly half of the total cost of a MOF product presently. Thus, following separation from the batch liquid, MOF crystals must be activated prior to use using a multi-step solvent exchange process that removes contaminants, partially reacted (or unreacted) products, and high-boiling solvents from the pores of the resulting MOFs—a slow and costly procedure.

Another disadvantage of conventional batch synthesis is the production of low-purity MOFs. Only a small fraction of a desired MOF product is produced. And, presence of secondary or interpenetration frameworks can exist within pores of a first framework, which are difficult to detect. Presence of secondary frameworks can block existing pores which affects properties of the resulting MOF. In addition, batch methods do not operate continuously, and have limited or no scalability, and as such are less likely to be cost-effective methods for MOF production. Batch methods used to produce MOF particles are also small or undersized, which limits potential applications or requires expensive post-processing to correct and are typically also very slow. Typical synthesis times are in excess of 24 hours on average and can be as long as 3 weeks or more.

Various methods have been proposed in the literature for combining MOFs with other functional matrix materials to form new multi-functional MOF composites that exhibit desired properties in order to broaden potential applications. However, controlling integration of the various and disparate individual components in suitable MOF composites is still undergoing. Thus, despite their tremendous potential, deployment of MOFs in commercial or industrial applications is currently limited by a lack of technologies and processes that permit synthesis and activation of these materials in suitable quantities, at desired quality and at costs that would make industrial applications feasible. New systems and processes are needed that address the various limitations of conventional syntheses and permit production of Metal Organic Frameworks (MOFs) and MOF composites on a large scale. The present invention addresses these needs.

SUMMARY OF THE INVENTION

The present invention provides a system and method for efficient scalable synthesis of Metal-Organic Frameworks (MOFs) materials including and MOF composites. In one embodiment the method for making Metal Organic Framework (MOF) materials including MOF composites, the method includes the step of injecting aerosolized MOF precursors into a fluidized bed reactor at a preselected temperature. Preferably this is done simultaneously and the combination of aerosolized dispersion of the MOF precursor into a fluid volume at a preselected temperature maintains consistency in particle formation which can then form the seeds for further growth. At the end of the desired MOF synthesis the temperature within the reactor can be raised to evaporate the residual solvent and densify the selected MOF products. In addition to providing effective and efficient MOF products the present invention also can be configured to recapture the MOF solvents which can then be recirculated and reused.

The simultaneous evaporation of the solvent within the fluidized bed reactor coupled with capture of the evaporated solvent as well as the ultrasonic aerosolization of the MOF precursors, and the fluidization of the MOF materials provide advantages in formation over the prior art. When the desired synthesis is complete the temperature in the reactor can be raised to remove any remaining solvents and densify the newly formed MOF material. These solvents can then be reused and recycled. Greater efficiencies can be obtained by continuously performing the method by introducing additional aerosolized MOF precursor droplets continuously into the fluid volume, while simultaneously heating, sonicating and recapturing solvents. This can be coupled to processes for removing materials or leaving them within the reactor in order for their size to increase. The present invention utilizes many MOF precursor materials. MOF precursors may include one or more metals selected from the group consisting of: Ti, V, Cr, Mn, Fe, Co, Ni, Cu, Zn, Y, Zr, Nb, Mo, Tc, Ru, Os, Rh, Pd, Ag, Au, Cd, Ir, Pt. and combinations thereof.

In addition the MOF precursors may include an organic linker selected from an aryl organic acid; an aryl alcohol; an aryl carboxylic acid; an aryl hydroxyl carboxylic acid; di-substitution products, tri-substitution products, and tetrasubstitution products thereof; or combinations thereof. The formed MOF or MOF composites are preferably between about 50 μm to about 1500 μm in size. The method of the present invention is also performed in an inventive system. In one embodiment of the invention the system includes a MOF production reactor that defines a fluidized bed reaction chamber configured to receive a plume of aerosolized MOF precursor droplets in a carrier gas therein for a time sufficient to form solid particles of the MOF or MOF composite of a selected size therein. The system may also include a heating device to alternatively raise and lower the temperature within the reaction chamber, an ultrasonic aerosolization device, a de-entrainment chamber configured to remove and collect solvents from the aerosolized MOF precursor droplets, a separation and recirculation device configured to collect the solid particles at the selected size from the MOF production reactor and to return the solid particles smaller that a preselected size back into the reaction chamber, and other pieces to assist in MOF formation. These items may have various names including a MOF production reactor (MPR) that includes an aerosolization, condensation, and evaporation (ACE) chamber configured to suspend a plume of aerosolized liquid MOF precursor droplets in a carrier gas and to circulate same in selected directions relative to the flow of the carrier gas, for example, parallel, orthogonal, or other selected angles at a selected temperature above ambient for a time sufficient to form solid particles of the MOF or MOF composite of a selected size therein. The MPR includes a MOF precursor solution introduction system that delivers MOF precursor solutions in a carrier gas into the MPR as a plume of aerosolized liquid droplets. The MPR further includes a de-entrainment (De-MOF) chamber configured to remove solvents from the aerosolized MOF precursor droplets therein that yields the MOFs and MOF composites formed in the MPR. Recovered solvents may then be recycled back into the MPR.

In one embodiment the method may include circulating the plume of aerosolized liquid droplets in the reaction chamber in a direction defined at a selected angle relative to the direction of flow of the carrier gas. For example, in some embodiments, the plume of aerosolized MOF precursor droplets is circulated in the fluid volume of the reaction chamber in a direction parallel to the direction of flow of the carrier gas. In some embodiments, the plume of aerosolized MOF precursor droplets is circulated in the fluid volume of the reaction chamber in a direction orthogonal to the direction of flow of the carrier gas. Carrier gases may include an inert gas or a mixture of an inert gas and one or more solvent vapors.

The method steps including introducing steps and circulating steps may be performed iteratively, for example, by introducing a fresh quantity of aerosolized MOF precursor droplets of a same or different MOF precursor solution continuously into the fluid volume of the reaction chamber to increase the size of the resulting solid particles of the MOF or MOF composite.

Forming solid MOFs and MOF composites in the ACE chamber can include condensing aerosolized MOF precursor droplets after releasing solvents therefrom at the reaction temperature to form seed particles of the MOF or MOF composite of a selected size. Size of the seed particles is typically about one micrometer. Solid seed particles formed in the ACE chamber provide sites for deposition and condensation of additional aerosolized MOF precursor droplets thereon of a same or different MOF precursor solution which increase the size of MOFs and MOF composites formed therein. Thus, in some embodiments, seed particles may comprise particles of a selected size, as detailed herein. In other embodiments, seed particles may comprise particles of non-MOF materials including, but not limited to, for example, metals, metal oxides, carbon, graphene, silicates, and other materials of a selected size that can also act as supports for growth of aerosolized MOF precursor droplets in the MPR, as detailed further herein. MOFs and MOF composites may be collected when selected particle sizes are reached.

Formation of MOFs and MOF composites can include removing (de-entraining) solvents as clean vapors from the MOF precursor aerosol droplets or from newly formed MOFs and MOF composites which can then be collected and recycled back to the MPR in various forms. Recycling the solvents can include introducing same into the MPR in the form of, for example, MOF precursor solutions, as make-up solvents, or as free solvents. The method may include forming solid particles of the MOF or MOF composites continuously.

In some embodiments, forming the solid particles includes a time of formation of at least about 1 minute. In some embodiments, forming the solid particles includes a time of formation of less than about 10 minutes. In some embodiments, forming the solid particles includes a time of formation of less than or equal to about 10 hours. In some embodiments, particles of the resulting MOFs or MOF composites are preferably selected between about 50 μm to about 1500 μm. The method may further include releasing the solid particles from the reaction chamber at the selected size to collect same and returning solid particles with sizes below the selected size back into the reaction chamber to increase the size thereof. In various embodiments, the method yields solid MOFs as products that are MOF composites, as detailed herein.

The present invention yields MOFs and MOF composites that are activated immediately upon formation without need for a solvent pre-treatment step to remove contaminates. Yields of MOFs and MOF composites are scalable. Optimized yields are greater than or equal to about 95%. For example, in some embodiments, yields are 99%.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

FIGS. 11C-11D show electronic mapping images for each of the metals of the mixed-metal MOF composite of FIG. 11A.

FIG. 11E presents EDX results for the mixed-metal MOF composite of FIG. 11A.

DETAILED DESCRIPTION

A system and process are detailed for continuous and controlled production of MOFs and MOF composites. The present invention overcomes previously unresolved problems, disadvantages, and limitations of conventional liquid batch processing including scalability, time to produce, low yields, low purity, lack of solvent recovery and recycling, activation, performance, and cost. In the following description, embodiments of the present invention are shown and described by way of illustration of the best mode contemplated for carrying out the invention. It will be apparent that the invention may include various modifications and alternative constructions. The present invention is intended to cover all such modifications, alternative constructions, and equivalents falling within the spirit and scope of the invention as defined in the claims. Accordingly, the description of the preferred embodiments should be seen as illustrative only and not limiting.

Figure 1:
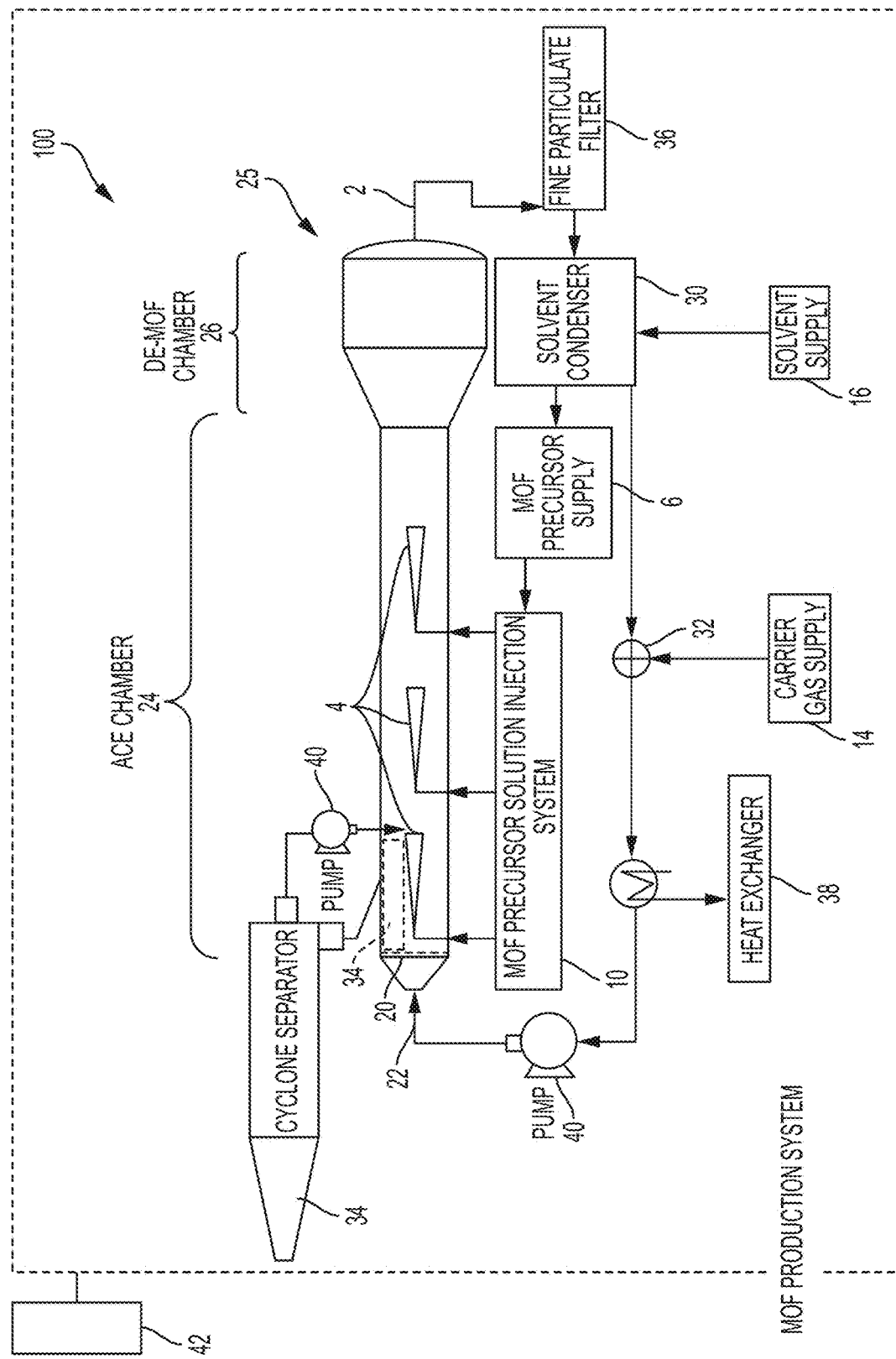
FIG. 1 shows a sample system for production of MOFs and MOF composites.

FIG. 1 shows one exemplary embodiment of a MOF production system 100 that allows for continuous and controlled production of MOFs and MOF composites as described in the disclosure. In this embodiment of the invention the system 100 includes a generally cylindrical MOF production reactor (MPR) 25 having a body that defines and internal volume sufficient to hold a fluidized bed reactor and to allow various method steps to occur. The capability and dimension of the internal volume is scalable to allow for scaled production of MOFs and MOF composites. In this exemplary embodiment, the MPR 25 body is a stainless steel vessel that defines an internal volume of ~5 liters. Within the MPR 25 a portion of the volume, called the ACE chamber 24 provides a location for aerosolization and condensation of MOF precursor solutions and evaporation of solvents to occur. In the illustrated embodiment this ACE chamber 24 includes a height (length) of about 24 inches (60.96 cm), a width of about 2 inches (5.1 cm). MOF precursor solutions in a carrier gas form a plume of aerosolized liquid droplets and enter into the ACE chamber through the MOF precursor solution injection system 10. Preferably the ACE chamber contains a fluid into which the MOF precursors are enveloped and which assists to maintain general uniformity among the size of the solvent droplets. As the MOF precursors enter into the ACE chamber a preselected elevated temperature evaporates the solvents from the aerosolized droplets at the selected reaction temperature which condenses the solid MOF seed particles. As additional MOF precursors are added to the ACE chamber the MOF seed particles continue to grow by continued condensation of newly added aerosol droplets of the MOF precursor solution onto existing seed particles, which increases the size of the MOF particles in the MPR. A more detailed drawing of this is shown in FIG. 2.

The evaporated solvents are released as clean vapors through an outlet 2. Unlike other systems these solvents can be recovered downstream and recycled again into the system. In the operation of the exemplary embodiment, 80% or more of solvents used in precursor solutions were recovered and recycled.

The introduction system 10 introduces aerosolized MOF precursor solutions into the ACE chamber (zone) 24 in an inert carrier gas. The introduction system combines the aerosolized MOF precursors, a carrier gas and gas/solvent mixtures from each of their respective sources. In the example shown this would include the MOF precursor supply 6, the solvent supply 16 and the solvent condenser 30 and the carrier gas supply 14. These are all plumbed and interoperably connected to an introduction system 10 that includes one or more introduction devices 4 that aerosolize MOF precursor solutions introduced into MPR 25 as a plume of aerosolized liquid droplets (aerosols) of preselected sizes, preferably ranging from anywhere from about 500 μm to about 2000 μm. Examples of such introduction devices 4 include, but are not limited to nebulizers; atomizers; misters; injectors; specialized nozzles, nuzzles and other similar devices and combinations. In the exemplary embodiment an ultrasonic aerosolizer was utilized to create and maintain aerosolized droplets.

The introduction system 10 utilizes one or more of such introduction devices 4 to introduce MOF precursor solutions into the MPR. Depending upon the needs of the user these ports may be variously configured to introduce a single MOF precursor solution into the MPR for synthesis of a single type of MOF, or multiple and different MOF precursor solutions into the MPR for synthesis of various MOF composites detailed herein. In the present illustrated embodiment the introduction system 10 is shown with three introduction devices 4 positioned at selected locations along the length of the MPR to create and control desired circulation patterns of MOF precursor solutions into the MPR. While this exemplary arrangement is shown it is not limiting and MOF precursor solutions can be introduced into the MPR in various directions and patterns depending upon the needs of the user and as detailed further herein. In the illustrated embodiment a distribution plate 20 is also a part of the introduction system and functions to assist in the delivery of a carrier gas and gas-solvent mixtures uniformly through the MPR. The distribution plate 20 may include a number of inlets through which MOF precursor solutions and carrier gasses are passed into the chamber and a circulating pattern of aerosolized liquid droplets are created and maintained.

In the exemplary embodiment, MOF precursor solution is introduced in a direction parallel to the flow of the carrier gas or gas-solvent mixture, for example, through the bottom or top of the reactor at a selected flow rate. However, direction is not limited, as shown. In various embodiments, MOF precursor solution is introduced in various directions at angles selected between about 0 degrees and about 180 degrees relative to the flow of the carrier gas or the gas-solvent mixture to create various circulation patterns for the aerosolized droplets of MOF precursor solution in MPR. Carrier gases used in concert with the present invention may be either inert or reactive and recovered solvent vapors and recovered carrier gases may be used to form a part of the carrier gas portion.

In the exemplary embodiment, flow rates for the carrier gas are selected from about 0.5 standard cubic feet per minute (scfm) to about 5.0 scfm, with a typical rate of about 2.0 scfm. Gas flow rates are selected that suspend and circulate MOF precursor solutions in ACE chamber in MPR. Gas flow rates are typically adjusted depending upon the size of the MOF particles. Preferred carrier gas flow rates are between about 5 times to about 10 times the minimum velocity needed to suspend MOF precursor solutions in the MPR. Higher velocities provide better suspension of MOF precursor solutions for continuous production of MOF particles in the MPR for selected applications. As the MOF precursors and the carrier gas pass through the fluidized bed reactor the particles coalesce in the reactor and fluidize. The deposition of the MOF precursors on the fluidized particles form seeds from which the MOF will form and develop. When the solvent is driven off these MOF will densify and be activated and ready for use.

In this embodiment of the invention a MOF de-entrainment chamber 26 couples to and is in gas (vapor) contact with ACE chamber 24 described previously. In the exemplary embodiment the de-entrainment chamber 26 is configured to decelerate MOF particles formed in ACE chamber particles so they are no longer suspended in the carrier gas. Deceleration of MOF particles serves to separate (de-entrain) MOF particles from solvent vapors and the carrier gas before the solvents and carrier gas exit the MPR. In this illustrated embodiment the velocity of circulating MOF particles reaching the de-entrainment chamber 26 decreases as the square of the cross-sectional area. In the exemplary embodiment, velocity decreases by a factor of [36÷9] or four (4) times compared to the velocity of MOF particles circulating in ACE chamber 24. De-entrained MOF particles drop, for example, to the bottom of ACE chamber 24 for collection when the MOF particles reach a selected or desired size, or continue to circulate and grow in ACE chamber, as detailed further herein.

MOF de-entrainment chamber 26 includes a diameter dimension that is generally 3 to 10 times larger than the diameter dimension of ACE chamber 24. Dimensions are selected to provide a selected density of, and minimum diameter for, MOF particles in MPR. In the exemplary embodiment, de-entrainment chamber 26 includes a height (length) dimension of about 12 inches (30.48 cm), a width dimension of about 6 inches (15.24 cm), and a wall thickness of about 0.25 inches (0.635 cm), respectively. Dimensions and internal volumes are scalable permitting scaled production of MOFs and MOF composites.

In some embodiments, solvents released as vapors from de-entrainment chamber 26 are condensed in a condenser 30 positioned downstream from MPR 25 into their liquid form. Condensed and recovered solvents may be returned through a line controlled by a control valve 32 (e.g., a 3-way control valve) and delivered, recirculated, or fed back into MPR 25 upon demand through introduction system 10. In some embodiments the recovered solvents may be stored in a solvent reservoir 6, and then be mixed into new MOF precursor solutions, or be recycled back into MPR as a make-up solvent, or otherwise re-introduced back into the MPR to minimize the quantity of solvents needed for continuous operation. In addition to the recovery of solvents, recovered carrier gases can also be reintroduced into MPR. In some embodiments, system 100 further includes a separation and recirculation device 34 that couples to ACE chamber 24, and assists to control and select the sizes of MOF particles formed in MPR 25. In this illustrated embodiment a cyclone separator is shown. Such devices find particular utility in for example, for industrial applications.

In the exemplary embodiment, separation device 34 separates streams of particles into two streams. In a first stream, MOF particles of a preselected or selected size (e.g., "right-sized" or "over-sized" particles) are removed from ACE chamber 24 for collection. In a second stream, MOF particles with a size below the selected size (termed "fines" or "under-sized" particles) are returned to ACE chamber 24 for continued growth via deposition of MOF precursors until a desired size or characteristic is reached. While in this exemplary embodiment this separation device 34 is positioned external to the MPR 25, but the invention is not intended to be limited thereto, such a device could be alternatively integrated within the ACE chamber 24. In some embodiments an in-line filter 36 positioned downstream from outlet 2 can be utilized to remove any fines or particulates if released in solvents from the MPR. However, filter 36 is an optional component given the clean distillation of solvents from MPR 25.

System 100 may also include a heat exchanger 38 that heats carrier gases or preheats condensed solvents recovered from MPR 25 prior to re-entry back into the MPR. Gases, solvents, and MOF precursor solutions may be delivered and introduced into the MPR at selected pressures in concert with one or more pumps 40 such as, e.g., HPLC pumps or other pumping means known to those of ordinary skill in the art. No limitations are intended. The system 100 may also include a computer control system to control the systems including the MOF precursor introduction system 10, opening and closing of outlets 2 and inlets 22, flow of solvents into and out of solvent condenser 30, opening and closing of control valve 32, flows into and out of heat exchanger 38, and recirculation of MOF particles in and out of separation and recirculation device 34.

Figure 2:
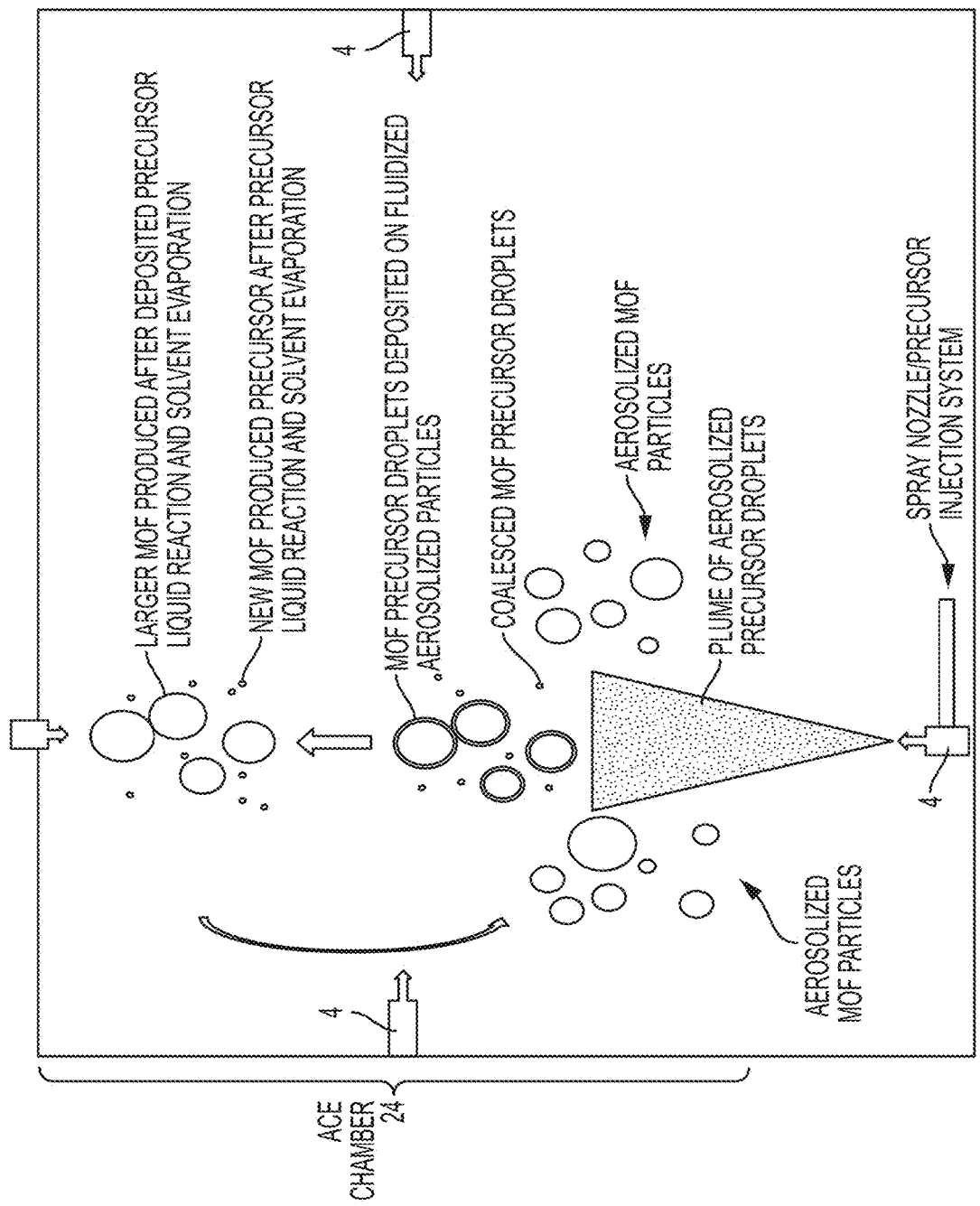
FIG. 2 illustrates an exemplary process for continuous production of MOFs and MOF composites, according to one embodiment of the process of the present invention.
Figure 3:
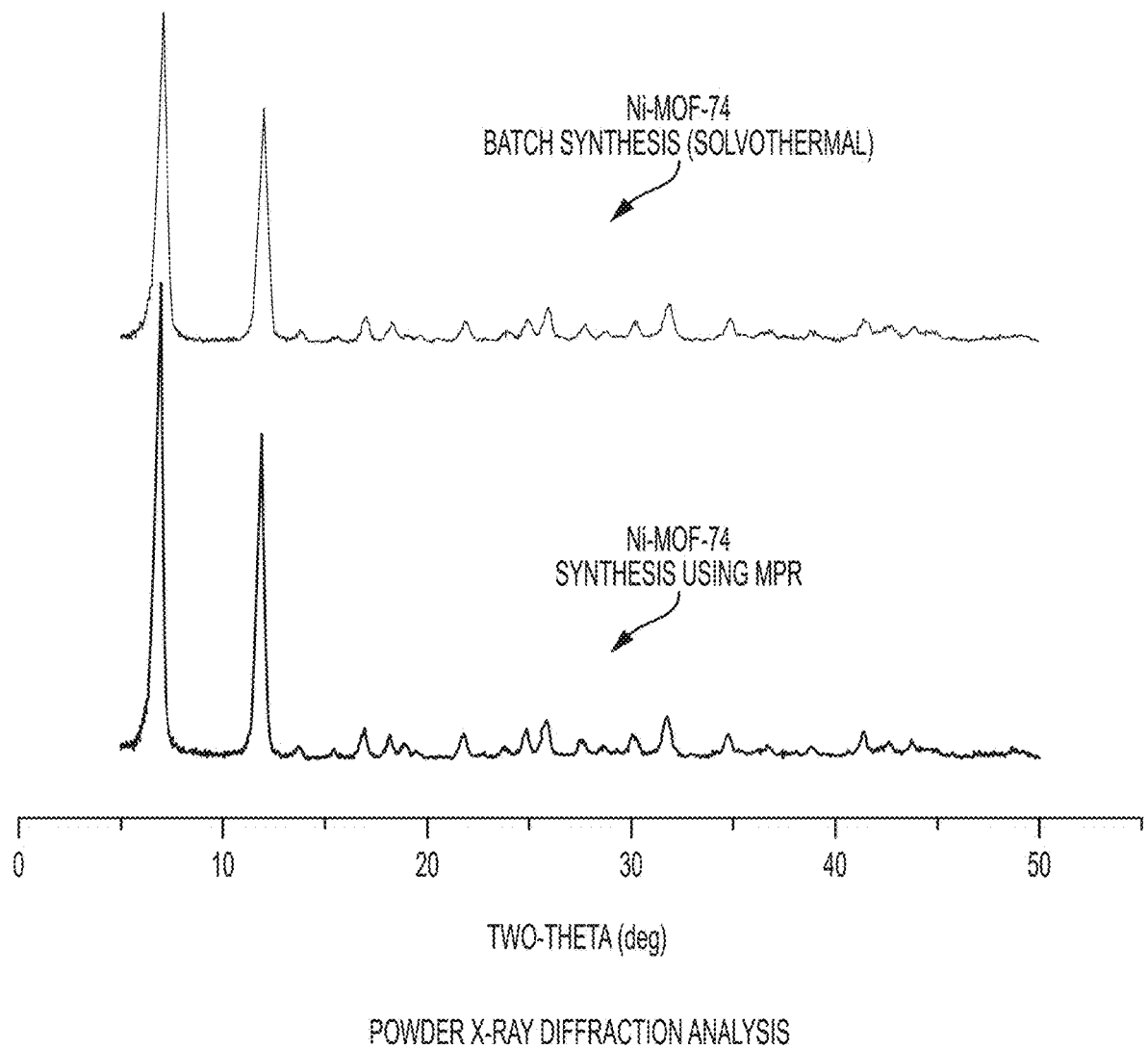
FIG. 3 compares XRD results for an exemplary pure MOF synthesized in accordance with the present invention against a MOF synthesized by conventional liquid batch processing.
Figure 4:
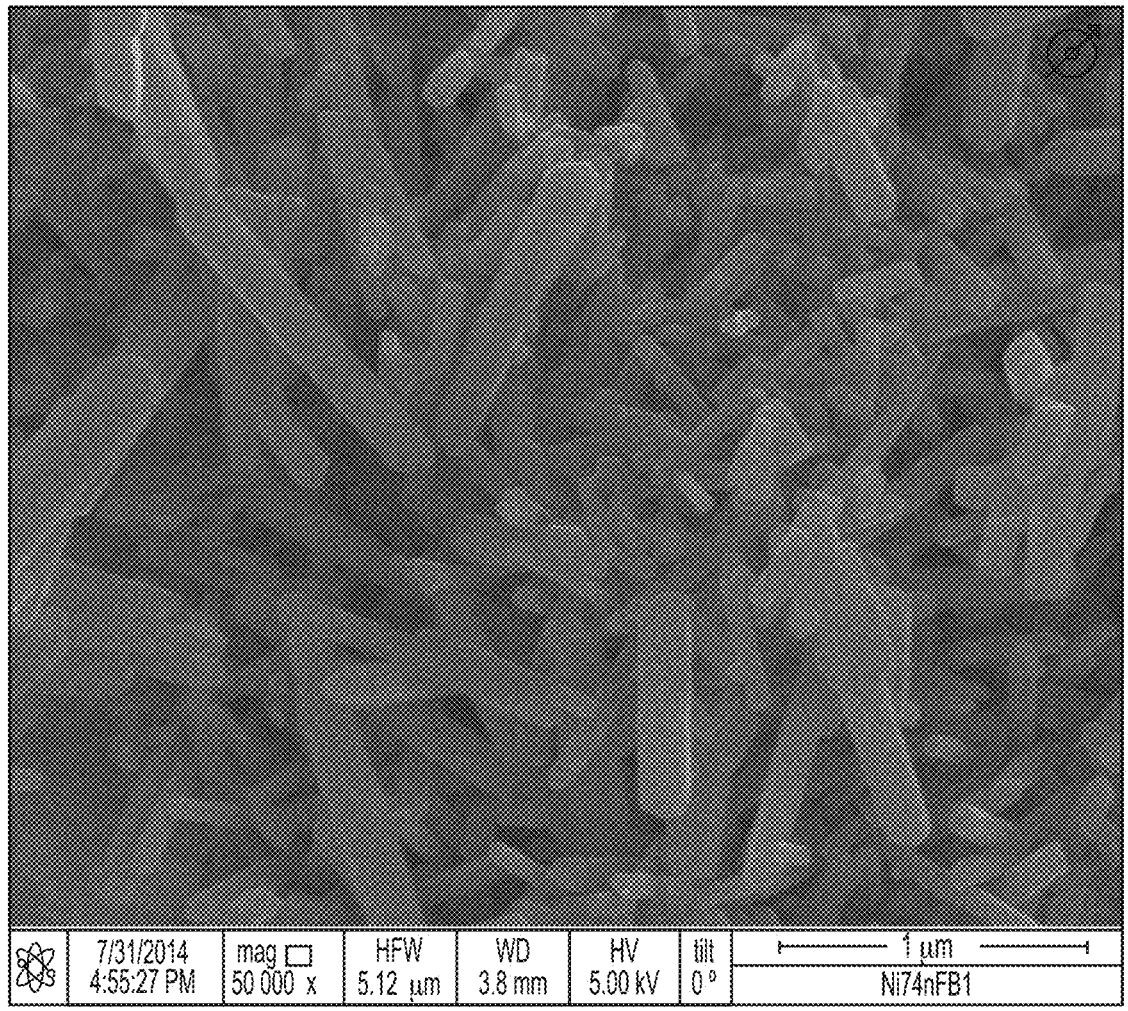
FIG. 4 is an SEM image of an exemplary pure MOF synthesized in accordance with the present invention FIG. 5 compares fractions of particles with selected sizes for an exemplary MOF synthesized in accordance with the present invention against a MOF synthesized by conventional liquid batch processing.
Figure 5:
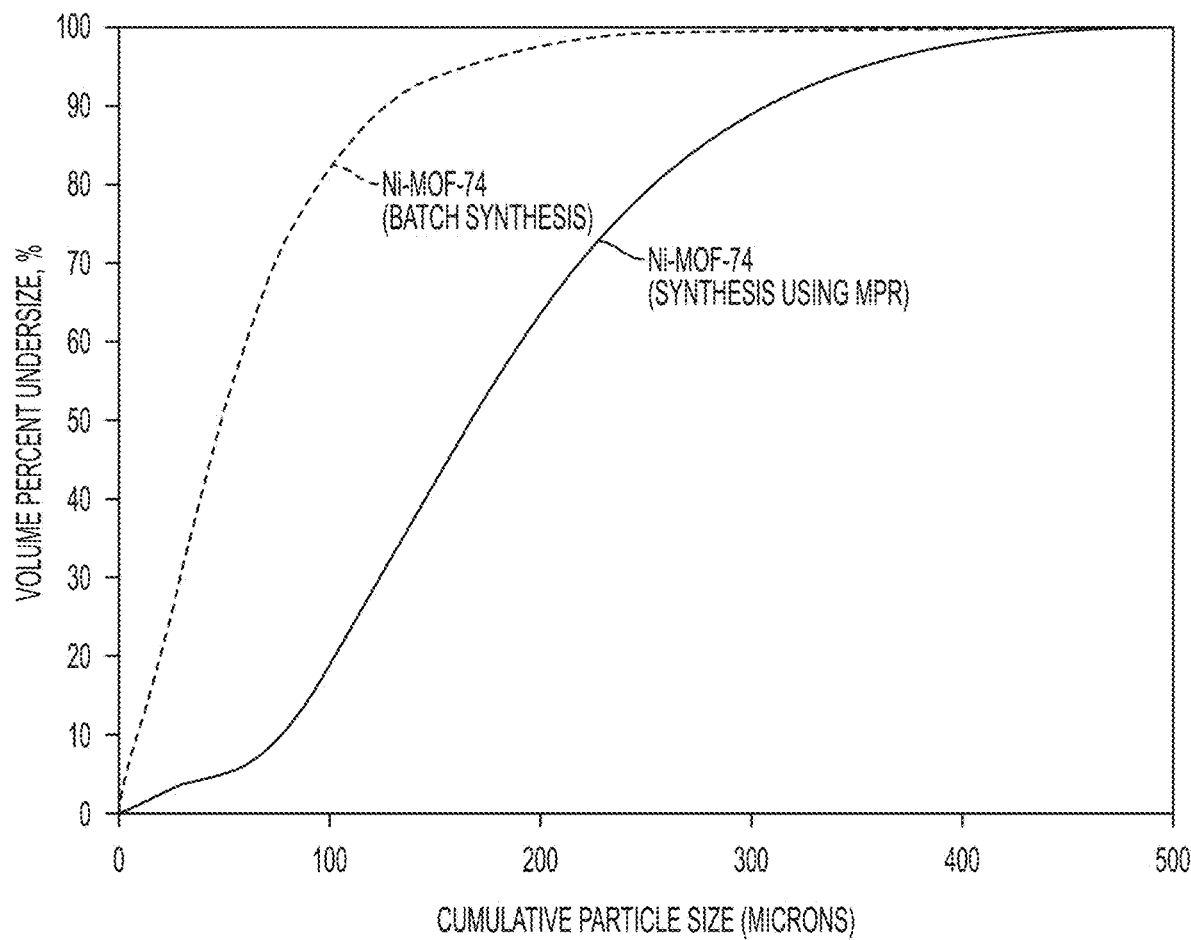
Figure 6:
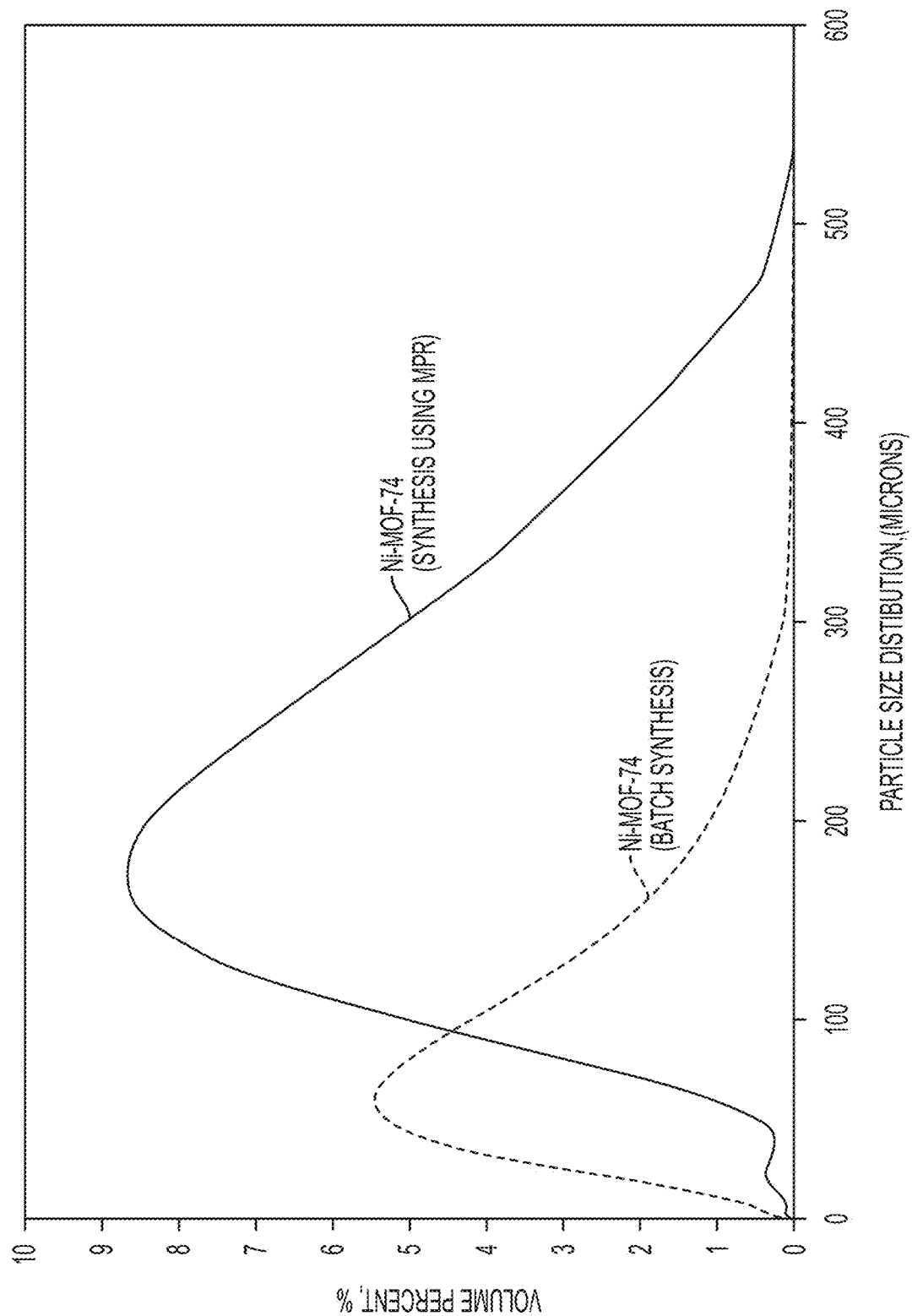
FIG. 6 compares distribution of particle sizes for an exemplary MOF of the present invention against a MOF product synthesized by conventional liquid batch processing.

FIG. 2 illustrates an exemplary process for continuous production of MOFs and MOF composites at superior yields. The process includes suspending a plume of aerosolized liquid droplets (aerosols) of a MOF precursor solution of a preselected size in a carrier gas in the vapor phase at a selected temperature in the ACE chamber (described previously in reference to FIG. 1) to form MOFs and MOF composites. As shown in the figure, MOF precursor solution can be introduced by introduction system (FIG. 1) into the ACE chamber (FIG. 1) in the MPR in various or selected directions with introduction devices 4 such as a nozzle properly positioned within the MPR. Introduction of MOF precursor solutions generates a plume of aerosolized precursor droplets of a desired or selected size. Aerosolized MOF precursor droplets are suspended in the carrier gas and circulated to maintain a uniform distribution of MOF precursor droplets in the fluidized bed reactor chamber. As the gasses circulate through the chamber fluidization occurs and this regulates the formation of the MOF materials that are developed. As this process progresses the chemical reagents introduced in the MOF precursor solutions coalesce in the MPR as solvents are removed from the aerosolized droplets, which yields the 3-D crystal structure of the resulting MOF or MOF composite formed in the MPR. Factors that control production of MOFs and MOF composites include, but are not limited to, for example, flow rates of MOF precursor solutions, carrier gases, and/or solvents into MPR; concentrations of reactants and other components in MOF precursor solutions, circulation rates of MOF aerosols; MOF particle density (p); and MOF particle sizes in MPR.

Solid MOF seed particles of typically a nanometer size will typically form initially. MOF seed particles continue to circulate in the MPR suspended in the carrier gas, which permits newly aerosolized droplets of the MOF precursor solution to condense onto the surface of the existing seed particles and for the MOFs to grow. Subsequent evaporation of solvent solidifies the new MOF precursor solution onto the existing seed particles, which adds a new layer or additional material that increases the size of the existing particles forming larger solid MOF particles. Solid MOF seed particles and larger MOF particles thus act as solid supports for continued growth of MOFs and MOF composites in the MPR. New MOF precursor solution is continuously introduced into the ACE chamber, which provides continuous production of new MOF seed particles and controlled production of MOF particles of preselected or selected sizes. MOF precursor solutions may have the same or different compositions to form a variety of different MOFs and MOF composites. MOF particles that achieve the selected or desired particle size may be collected and removed from the ACE chamber, for example, with a separation and recirculation device described previously in reference to FIG. 1.

FIGS. 3-6 show a variety of comparisons between the MOF products created in the present invention and the MOF products created by prior art processes. FIG. 3 compares XRD results for an exemplary nickel-based MOF product, Ni-MOF-74, synthesized in accordance with the present invention against the corresponding product produced by conventional liquid batch synthesis. Results show the MPR-synthesized MOF product is identical to the conventional product. However, MOF yields provided by the present invention are superior as discussed further herein. FIG. 4 shows an SEM image of an exemplary pure MOF synthesized in accordance with the present invention FIG. 5 compares cumulative fractions (volume %) of particles of selected sizes for an exemplary MOF (i.e., Ni-MOF-74) synthesized in accordance with the present invention against a conventional batch-synthesized product. Results show MOFs of the present invention have a cumulative particle size significantly greater compared to the batch synthesized product. And, sizes are selectable. The batch-synthesized product is not. FIG. 6 compares the distribution of particles of various sizes for the exemplary Ni-MOF-74 product of the present invention against the batch-synthesized product. Data in FIG. 6 again shows that particles of the MPR-synthesized Ni-MOF-74 (i.e., preselected or controlled) product have a mean particle size of ~200 microns compared to the mean particle size for the batch-synthesized (uncontrolled) particles of only 50 microns. In addition, Ni-MOF-74 particles of the present invention do not require solvent purification following synthesis.

The reaction kinetics of the present invention are superior to conventional liquid batch processing and provide a significant advantage. In a typical synthesis of a pure metal MOF (e.g., Ni-MOF-74), for example, the present invention forms MOF particles of a 20 micron size in a typical time of 1 minute or better compared to 24 hours for conventional liquid batch synthesis. These exemplary MOF production results correspond to a surprising improvement in reaction kinetics of at least about 1440 times, or 4 orders of magnitude. The yields of the MOFs and MOF composites are scalable. Unoptimized yields of MOFs and MOF composites are typically greater than or equal to about 35%, however with optimization yields anywhere from 60% to 99% are possible. MOFs and MOF composites generated under this process also have a superior purity due to an absence of reactant contamination. Again purity percentages vary from 60% to 99% or better.

The materials, rates and conditions for operation of the present invention can vary widely and can be specifically tailored to meet the needs of a particular user. The examples and information provided here after therefore should be understood as exemplary only and not as limiting as to the scope of the invention. As a party of skill in the art will recognize, various alternative and modifications to the present invention can be made without detracting from the spirit and scope of the invention as set forth in the claims.

Table 1 shows exemplary parameters for synthesizing various pure metal MOFs in accordance with the present invention.

TABLE 1

| MOF Type | Precursors | Ligand: Metal Salt Ratio [Mole:Mole] | Solvent |
|---|---|---|---|
| MOF-74 (Ni, Co, Zn, Mn, Fe, Ti, Mg, Cu,) | [DHTA:metal nitrate] | [1:3.3] | [DMF:Ethanol:Water] [1:1:1 to 15:1:1] |
| MOF-74 (Ni, Zn, Co, Mg, | [DHTA:metal acetate] | [1:2] | [THF:Water] [1:1] |

TABLE 1-continued

| MOF Type | Precursors | Ligand: Metal Salt Ratio [Mole:Mole] | Solvent |
|---|---|---|---|
| Mn, Fe, Cu) | | | |
| MOF-5 | [TPA:Zn acetate] | [1:2.2] | DMF |
| IRMOF-3 | [2-Amino TPA:Zn Nitrate (hexahydrate or tetrahydrate)] | [1:3] | DMF |
| IRMOF-9 | [4,4'-biphenyldicarboxylic acid:Zn nitrate (hexahydrate or tetrahydrate)] | [1:5.5] | DMF |
| MOF-177 | [BTB:Zn Nitrate (hexahydrate or tetrahydrate)] | [1:9] | DEF |
| MOF-180 | [BTE:Zn nitrate (hexahydrate or tetrahydrate)] | [1:16] | [DEF:NMP] [1:1] |
| MOF-200 | [BBC:Zn acetate] | [1:10] | [DEF:NMP] [1:1] |
| MOF-210 | [BTE:BPDC:Zn acetate] | [1:2] | [DEF:NMP] [1:1] |
| HKUST-1 | [Benzene-1,3,5-tricarboxylic acid:Cu nitrate (or Cu acetate)] | [1:2] | [DMF:EtOH:$H_2O$] [1:1:1] |
| ZIF-8 | [2-methylimidazole:Zn nitrate (hexahydrate or tetrahydrate)] | [1:1] | DMF or $H_2O$ or MeOH |
| TetZB | [tetrakis[4-(carboxyphenyl)-oxamethyl] methane; bipyridine:Zn nitrate (hexahydrate or tetrahydrate)] | [1:1:1] | [DMF] |
| MOF-801 | [Fumaric acid:Zr oxychloride] | [1:1] | [DMF:Formic Acid [3:1] |
| MOF-802 | [Pyrazole-3,5-dicarboxylic acide:Zr oxychloride] | [1:1] | [DMF:Formic Acid [1.5:1] |
| MOF-805 | [1,5-Dihydroxynaphthalene-2,6-dicarboxylic acid:Zirconyl chloride (octahydrate)] | [1:2] | [DMF:Formic Acid [5:1] |
| MOF-808 | [1,3,5-benzenetricarboxylic acid:Zirconyl chloride (octahydrate)] | [1:1] | [DMF:Formic Acid [1:1] |
| MOF-812 | [4,4',4'',4'''-Methanetetrayltetra-benzoic acid:Zr oxychloride] | [1:2] | [DMF:Formic Acid [1.5:1] |
| MOF-841 | Benzenetribenzoic acid:zirconyl chloride (octahydrate)] | [1:4] | [DMF:Formic Acid [1.5:1] |
| DUT-52-M (M = Zr or Hf) | [Napthalene-2,6-dicarboxylic acid:Metal (M) chloride (where M = Zr or Hf) | [0.75:1] | [DMF:Acetic Acid] [15:1] |
| DUT-67 | [Thiophene-2,5-dicarboxylic acid:Zirconyl chloride (octahydrate)] | [2:3] | [DMF:Formic Acid] [1.8:1] |
| UIO-66 | [TPA:Zirconyl chloride (octahydrate)] | [1:0.75] | DMF (acidified)* |
| UIO-67 | [Biphenylene dicarboxylic acid:Zr chloride] | [1:0.9] | DMF (acidified)* |
| UIO-68 | [Triphenylene dicarboxylic acid:Zr chloride] | [1:0.5] | DMF (acidified)* |
| NU-1000 | [1,3,6,8-tetrakis(p-benzoic acid) pyrene ($H_4$TBAPy):Zirconyl chloride (octahydrate)] | [1:10] | DMF |
| SIM-1 | [4-methyl-5-imidazolecarboxaldehyde:Zn acetate (dehydrate)] | [4:1] | DMF |
| MIL-100 (Cr, Fe) | Benzene-1,3,5-tricarboxylic acid:Cr nitrate or Fe nitrate] | [1:1.1] | $H_2O$ |
| MIL-101 (Cr) | [TPA:Cr nitrate] | [1:1] | $H_2O$ |
| Bio-MOF-1 | [Adenine:4,4'-biphenyl dicarboxylic acid:Zn acetate (dehydrate)] | [1:2.3] | DMF:$H_2O$ [6:1] |
| ZMOFs | ditopic N-donor linking agents such as pyrimidine-, imidazole-, and tetrazole-based linkers and transition metals | Various Ratios | DMA, DMF, other solvents, and combinations of solvents |
| SIFSIX-3-M (M = Co, Ni) | [metal silicofluoride:pyrazine] | [1:2] | MeOH |

Precursors: BBC = 4,4',4''-[benzene-1,3,5-triyl-tris(benzene-4,1-diyl)]tribenzoate; BTB = Benzene tribenzoic acid; BTE = 4,4',4''-[benzene-1,3,5-triyl-tris(ethyne-2,1-diyl)] tribenzoate; BPDC = biphenyl-4,4'-dicarboxylate; DHTA = DihydroxyTerepthalic Acid; TPA = Terepthalic Acid.
Solvents: DMF = N,N-dimethylformamide; DEF = N,N-diethylfromamide; EtOH = ethanol; $H_2O$ = water; NMP = N-Methyl-2-pyrrolidone; THF = Tetrahydrofuran.
*(acidified) = 2 drops of HCl (1M).

Other pure metal MOFs include, but are not limited, for example, NU-100; MIL-53; MIL-120; porous hexacyano materials (e.g., Prussian Blue); and metal nitroprussides.

composites, as demonstrated further herein. The following Table 2 lists exemplary MOF composites with exemplary precursors.

| MOF Composite | Precursors [Ratio] | Solvents [Ratio] |
|---|---|---|
| Core-Shell or Yolk-Shell MOF Composites | | |
| Various MOFs (shell); Carbon (core) | [Core: activated carbon, carbon fibers, carbon nanotubes, porous carbon, or graphene oxide] [Shell: MOF precursors] | Solvent combinations from TABLE 1. |
| Various MOFs (shell); Metals or Metal oxides (core) | [Core: metals, metal oxides, metal nanoclusters] [Shell: MOF precursors] | Solvent combinations from TABLE 1. |
| Various MOFs (shell); Pre-synthesized MOFs (core) | [Core: pre-synthesized MOFs particles] [Shell: MOF precursors] | Solvent combinations from TABLE 1. |
| Various MOFs (shell); gypsum (core) | [Core: gypsum particles] [Shell: MOF precursors] | Solvent combinations from TABLE 1. |
| Exemplary MOF Composites | | |
| M-MOF-74 (shell); Iron oxide, gypsum, or activated carbon (core); (M = Ni, Co, Zn, Mg, Cu, Fe, and Mn) | [Core: Iron oxide or gypsum] [Shell: DHTA:Metal nitrate/acetate] [1:2] | For metal nitrate: DMF:EtOH:$H_2O$ [1:1:1] For metal acetate: THF:$H_2O$ [1:1] |
| M-MOF-74 (shell); Cr-MIL-101(core); (M = Ni, Co, Zn, Mg, Cu, Fe, Mn) | [Core: MIL-101] [Shell: DHTA:Metal nitrate/acetate] [1:2] | For metal nitrate: DMF:EtOH:$H_2O$ [1:1:1] For metal acetate: THF:$H_2O$ [1:1] |
| $M_1$-MOF-74 (shell); $M_2$-MOF-74 (core) ($M_1$ and $M_2$ = Ni, Co, Zn, Mg, Cu, Fe, Mn) | [Core: Co-MOF-74] [Shell: DHTA:Metal nitrate/acetate] [1:2] | For metal nitrate: DMF:EtOH:$H_2O$ [1:1:1] For metal acetate: THF:$H_2O$ [1:1] |
| M-MOF-74(shell); MIL-53 (core) (M = Ni, Co, Zn, Mg, Cu, Fe, Mn) | [Core: MIL-53] [Shell: DHTA:Metal nitrate/acetate] [1:2] | For metal nitrate: DMF:EtOH:$H_2O$ [1:1:1] For metal acetate: THF:$H_2O$ [1:1] |
| Mixed-Metal MOF Composites | | |
| $M_1$-$M_2$-MOF-74 ($M_1$-$M_2$ = Ni, Co, Zn, Mg, Cu, Fe, and Mn) | [DHTA:Metal nitrate/acetate] [1:2] | For metal nitrate: DMF:EtOH:$H_2O$ [1:1:1] For metal acetate: THF:$H_2O$ [1:1] |

Precursors: DHTA = DihydroxyTerepthalic Acid.
Solvents: DMF = N,N-dimethylformamide; DEF = N,N-diethylfromamide; EtOH = ethanol; $H_2O$ = water; THF = Tetrahydrofuran.

The method and system of the present invention can be utilized to generate not only the MOFs discussed above but also MOF composites. The term MOF products as used in this application refers to both MOFs as well as molecular structures that incorporate various chemical components introduced into the MPR in selected MOF precursor solutions or as dry powders that are incorporated into the structure of the metal organic framework of the MOF composite. MOF composites that can be synthesized in accordance with the present invention are not limited. MOF composites include, but are not limited to, for example, core-shell MOF composites; yolk-shell MOF composites; segmented MOF composites; doped MOF composites; mixed-metal (heterometallic) MOF composites; and mixed-linker MOF composites.

Exemplary MOF composites synthesized in accordance with the present invention include, for example, core shell composites including, for example, Ni-MOF-74 (shell)/carbon (core); Ni-MOF-74 (shell)/Cr-MIL-101 (core); Ni-MOF-74 (shell)/Co-MOF-74 (core); Ni-MOF-74(shell)/MIL-53 (core); and mixed-metal MOF composites including, for example, Ni—Zn-MOF-74. However, the invention is not intended to be limited to these exemplary MOF composites, as demonstrated further herein. The following Table 2 lists exemplary MOF composites with exemplary precursors.

Figure 7A:
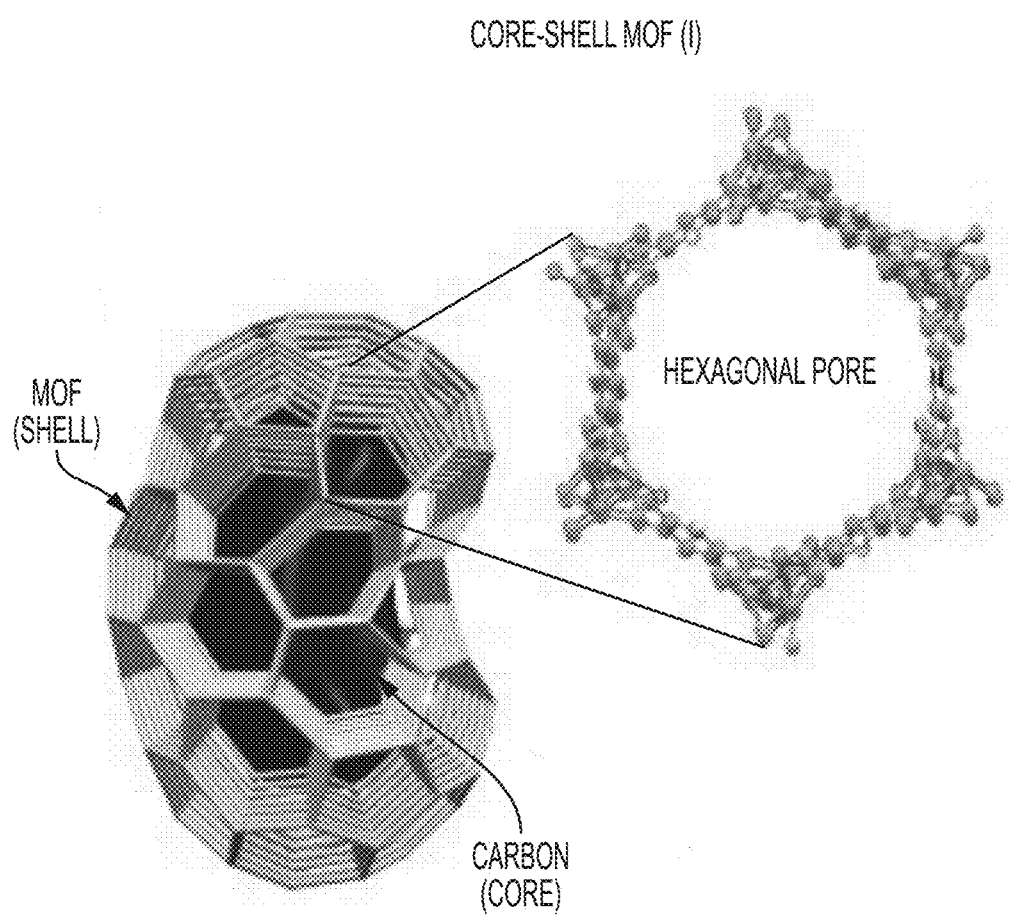
FIG. 7A is a pictograph illustrating a layered structure of an exemplary core-shell MOF composite of the present invention.
Figure 7B:
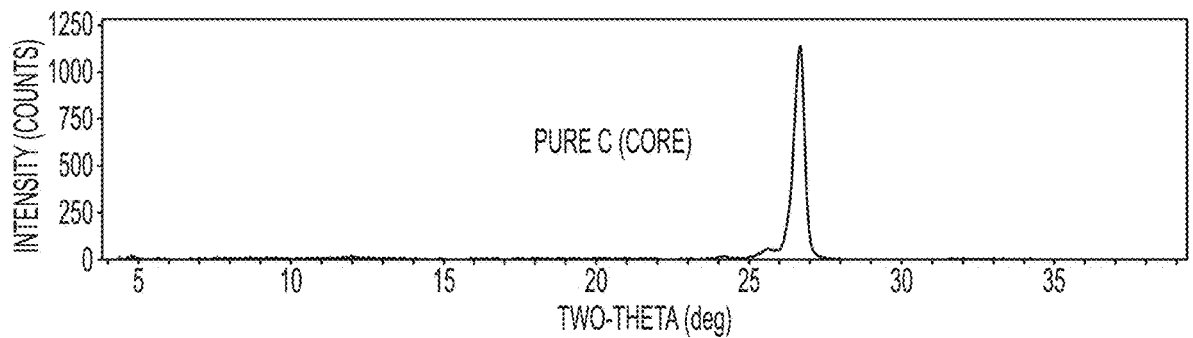
FIGS. 7B-7D show XRD results for the MOF composite of FIG. 7A.
Figure 7C:
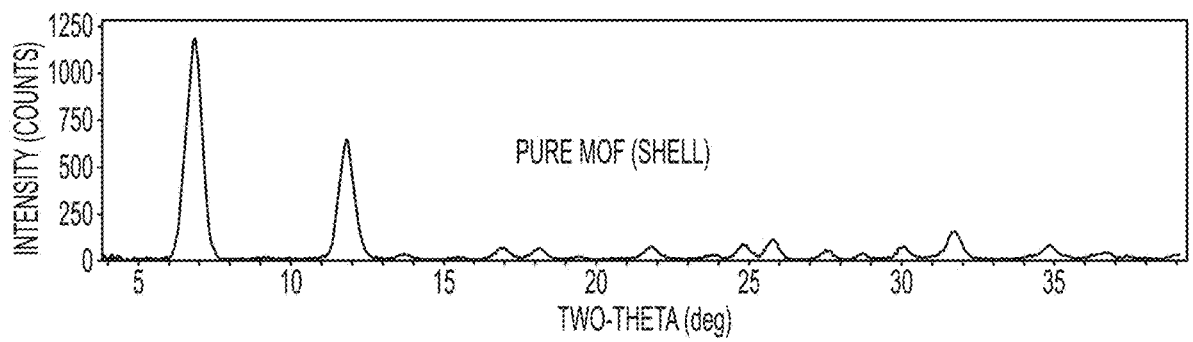
Figure 7D:
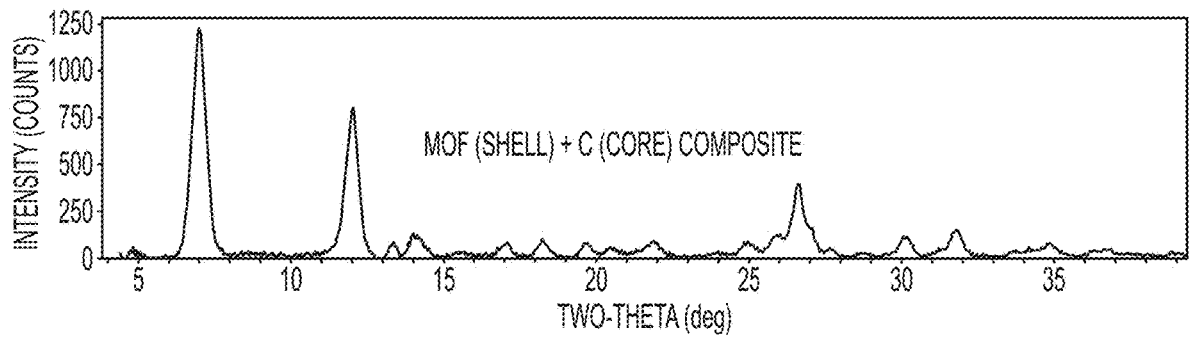
Figure 7E:
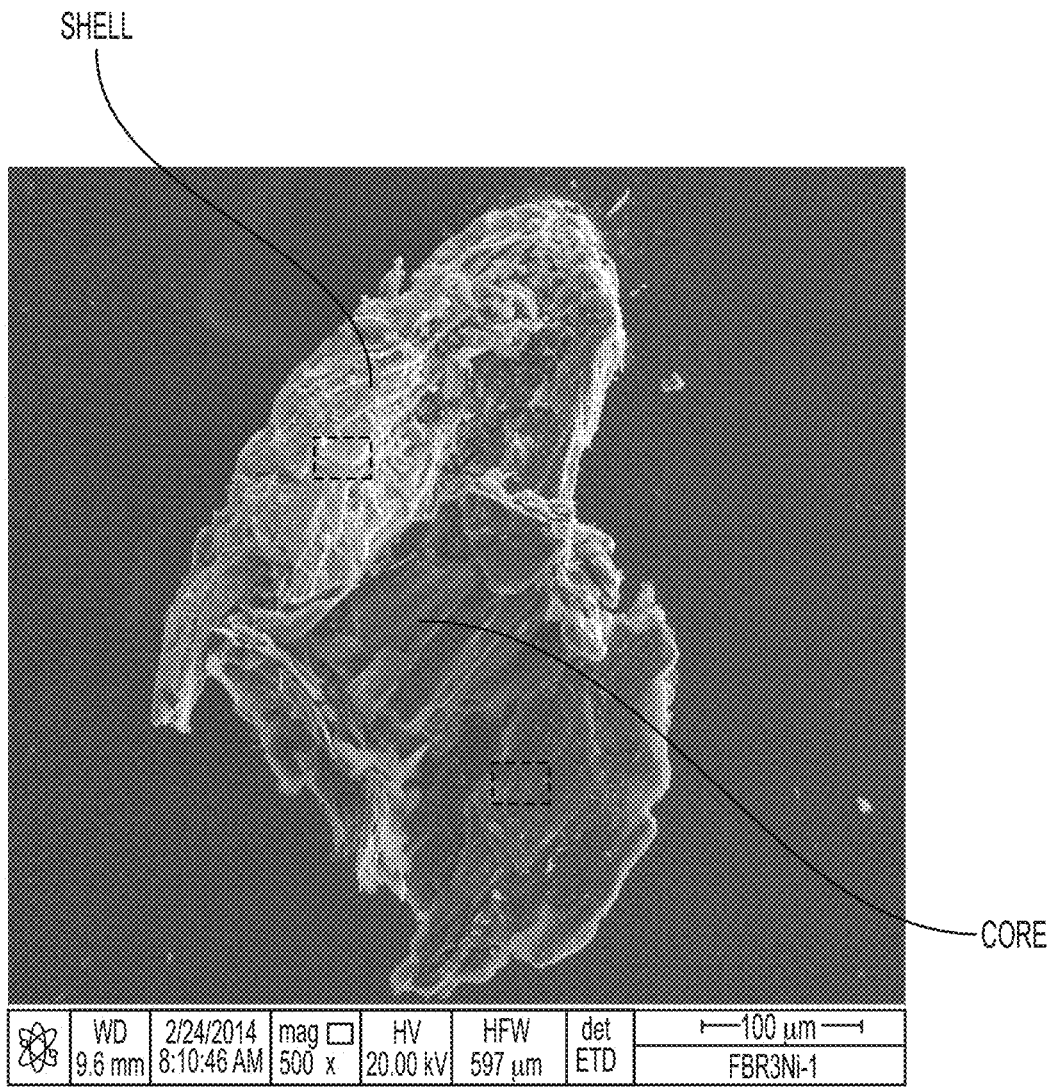
FIG. 7E is an SEM image of the exemplary core-shell MOF composite of FIG. 7A.
Figure 7G:
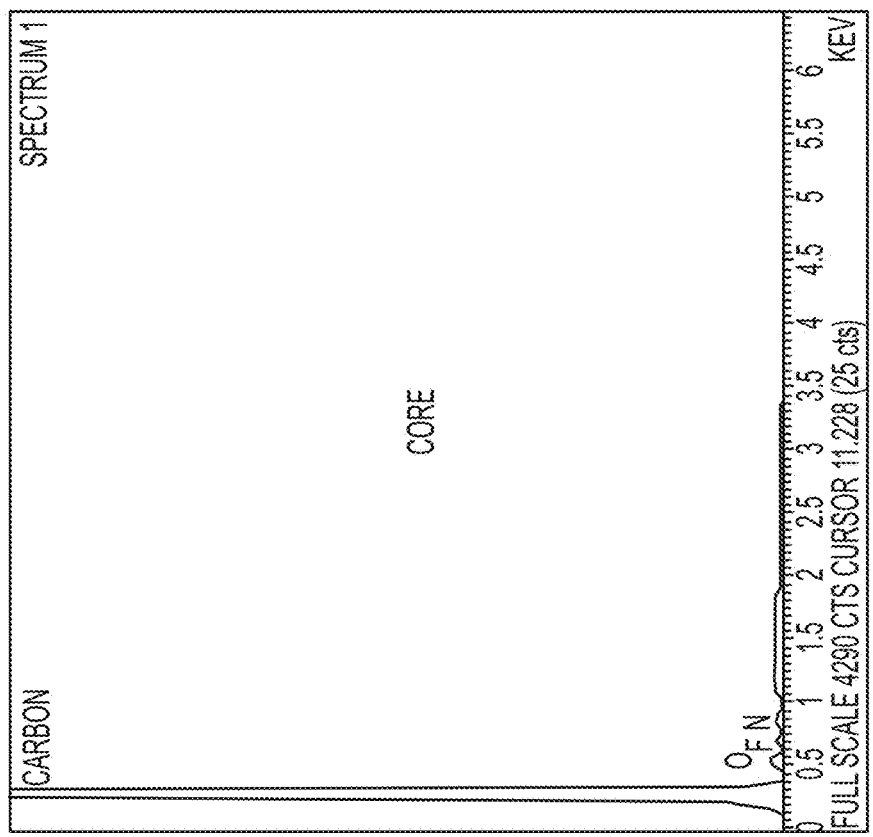
FIGS. 7F-7G show EDX results for components of the core-shell MOF composite of FIG. 7A.
Figure 7F:
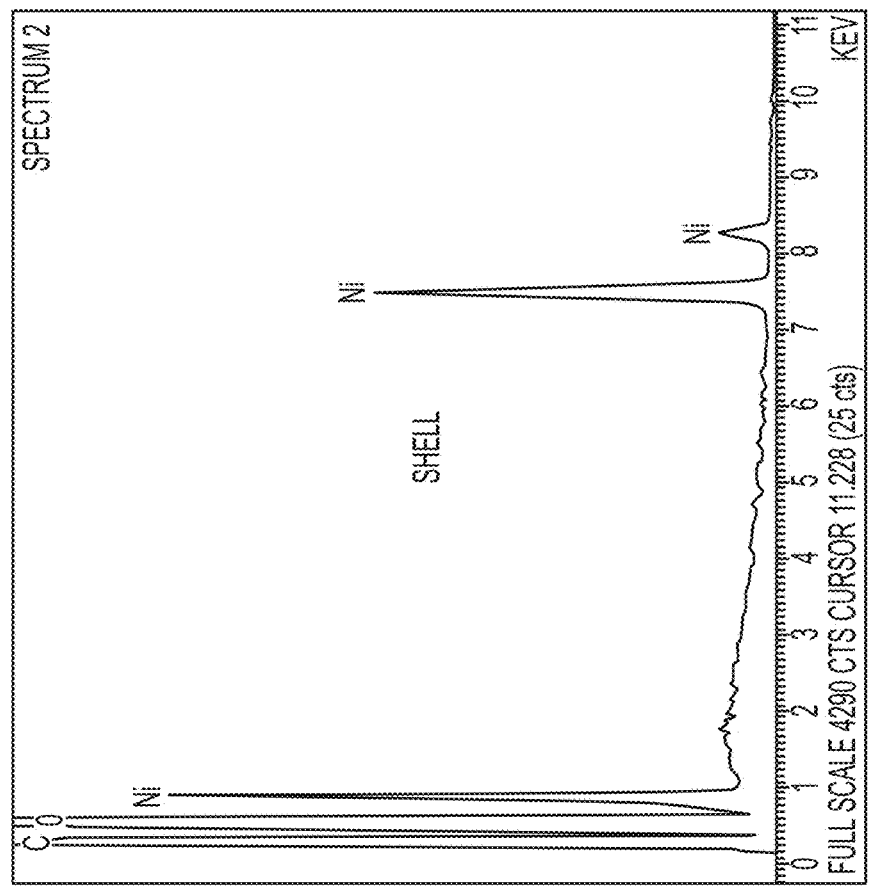

FIG. 7A is a pictograph illustrating an exemplary core-shell MOF composite of the present invention. The MOF composite includes a carbon core and a shell of a nickel-containing MOF (i.e., Ni-MOF-74). The shell of the MOF composite may include any number of shell layers, from one to many. MOF core-shell composites synthesized in accordance with the present invention may be characterized using various analytical techniques including, for example, powdered X-ray Diffraction (XRD) analysis, Scanning-Electron Microscopic imaging (SEM), Energy-Dispersive X-ray (EDX) analysis as detailed hereafter. FIGS. 7B-7D show XRD results for the components of the MOF composite illustrated in FIG. 7A. For example, FIG. 7B shows XRD results for pure carbon. FIG. 7C shows XRD results for the pure nickel-metal MOF (Ni-MOF-74). And, FIG. 7D shows XRD results for the MOF composite that shows the composite includes both the (Ni) metal of the pure Ni-containing MOF of the shell and the carbon (C) within the core as structural (crystalline) components of the MOF composite. FIG. 7E presents an SEM image of the exemplary core-shell MOF composite of FIG. 7A showing the target location of probe beams for a subsequent EDX analysis described hereafter. The SEM image shows that the Ni-MOF-74 shell formed atop the carbon core. FIG. 7F presents EDX results for the Ni-MOF-74 shell at the target location of the MOF composite showing the presence of Ni metal. FIG. 7G presents EDX data for the core of the MOF composite showing the presence of a high-intensity signal peak for carbon indicating presence of carbon within the core of the MOF composite.

Figure 8A:
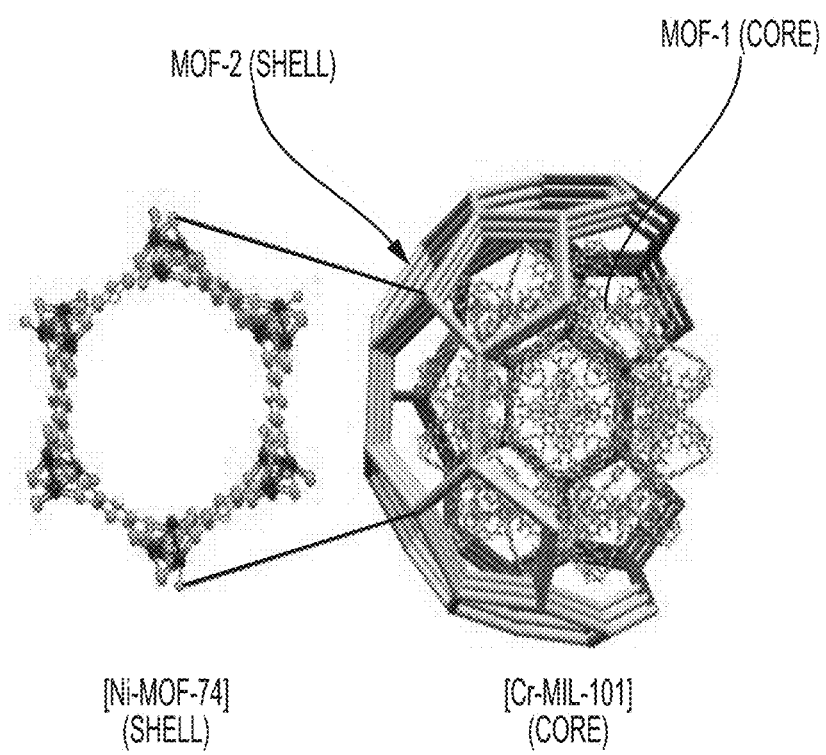
FIG. 8A is a pictograph illustrating a layered structure of another exemplary core-shell MOF composite of the present invention.
Figure 8B:
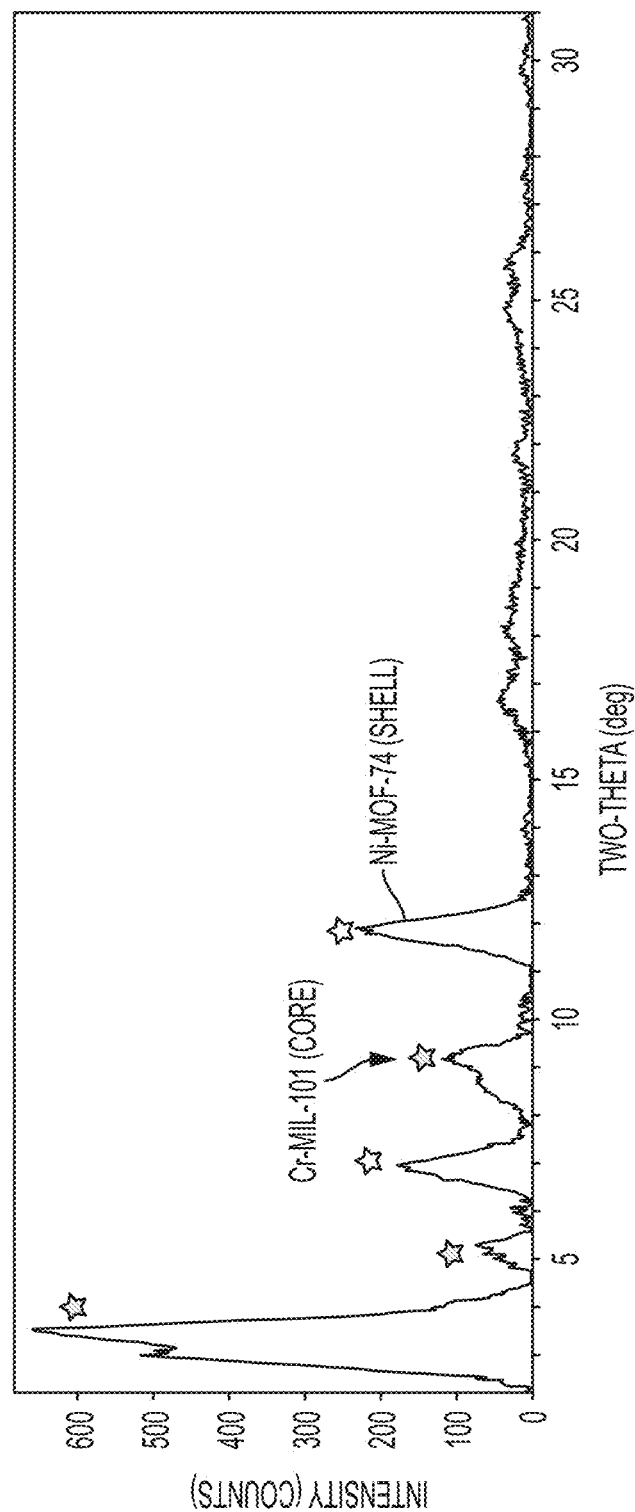
FIG. 8B shows XRD results for the MOF composite of FIG. 8A.
Figure 8C:
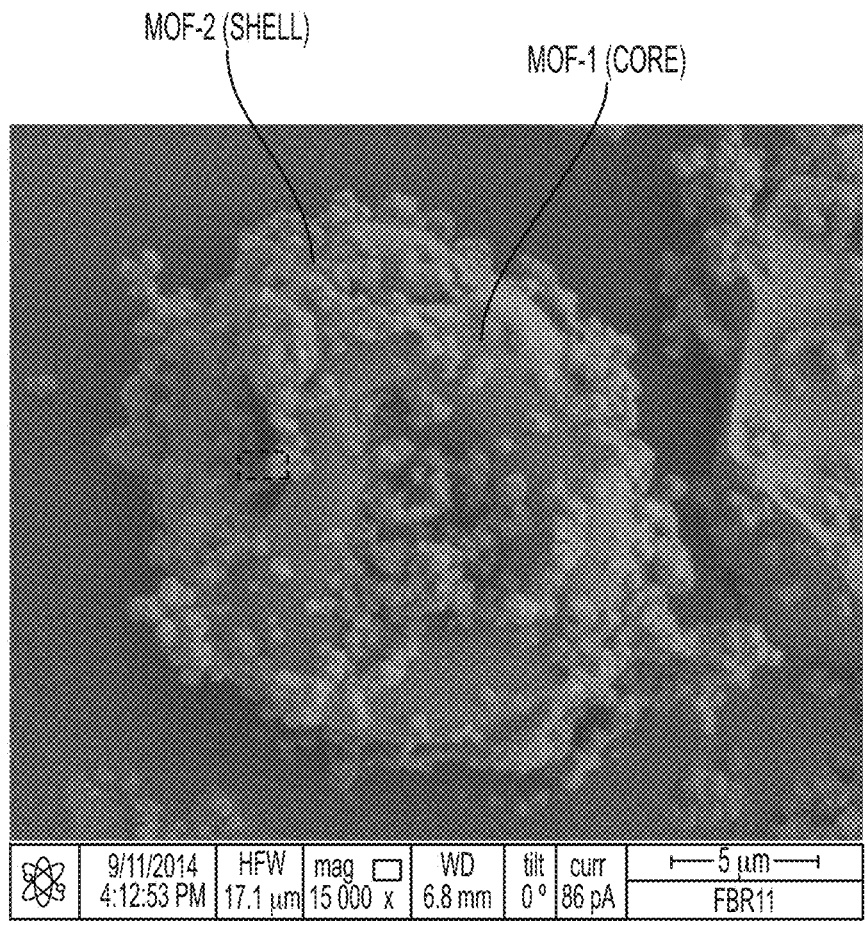
FIG. 8C is an SEM image of the core-shell MOF composite FIG. 8A.
Figure 8D:
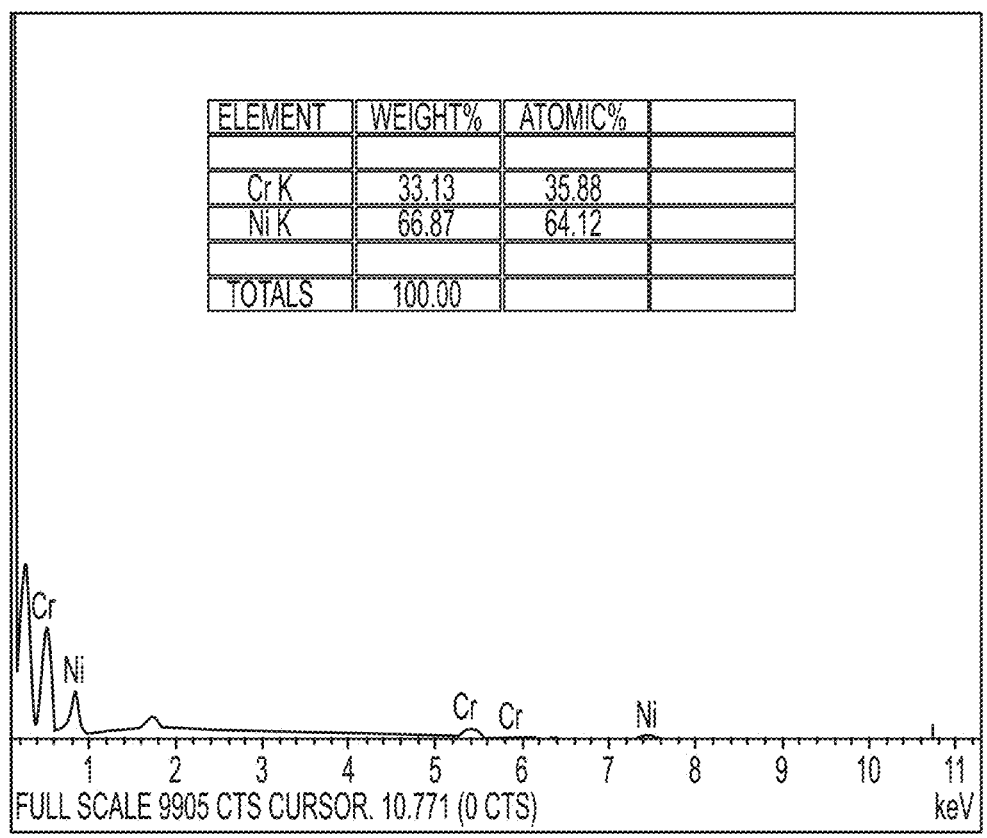
FIG. 8D shows EDX results for the MOF composite of FIG. 8A.

FIG. 8A is a pictograph illustrating another exemplary core-shell MOF composite created under the process of the present invention. The composite includes a core comprised of a first chromium (Cr)-containing MOF (e.g., Cr-MIL-101), and a second Ni-containing MOF (e.g., Ni-MOF-74) as the shell of the MOF composite. The pictograph again illustrates that the MOF composite may contain any number of shell layers, from one to many. FIG. 8B presents powdered XRD data for the MOF composite of FIG. 8A showing presence of crystalline phases for both the core (e.g., Cr-MIL-101) and shell (e.g., Ni-MOF-74) of the MOF composite. FIG. 8C shows an SEM image of the MOF composite of FIG. 8A showing both the core and the shell, and the target location for the probe beam for an EDX analysis described hereafter. FIG. 8D presents EDX results for the composite of FIG. 8A showing the presence of both Cr metal in the core and Ni metal in the shell of the composite with their corresponding signal intensities demonstrating proper formation of the MOF composite.

Figure 9:
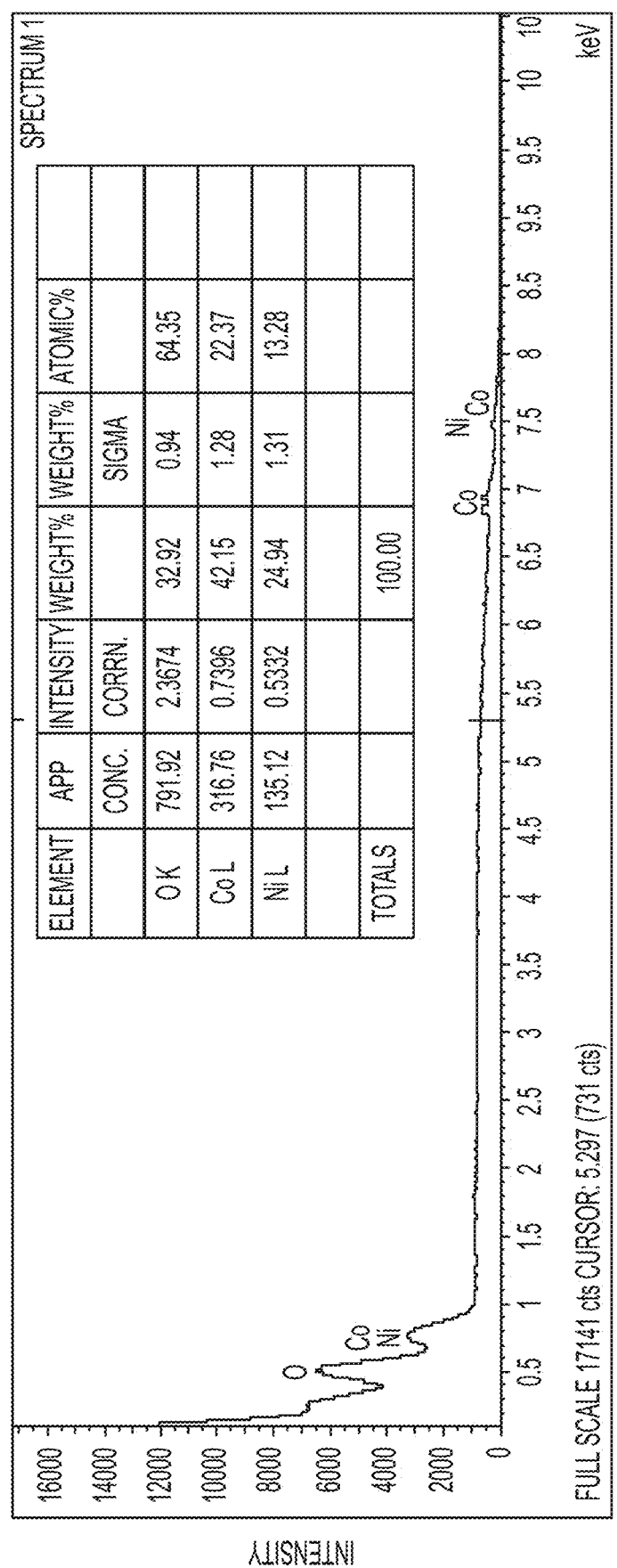
FIG. 9 shows EDX results for yet another exemplary core-shell MOF composite of the present invention.

FIG. 9 presents EDX data for yet another exemplary core-shell MOF composite of the present invention. The MOF includes a core of a cobalt (Co)-containing MOF (e.g., Co-MOF-74) and a shell of Ni-MOF-74. EDX data show both the presence of the Co metal in the core and the Ni metal in the shell of the composite with their respective signal intensities demonstrating the formation of the MOF composite.

Figure 10A:
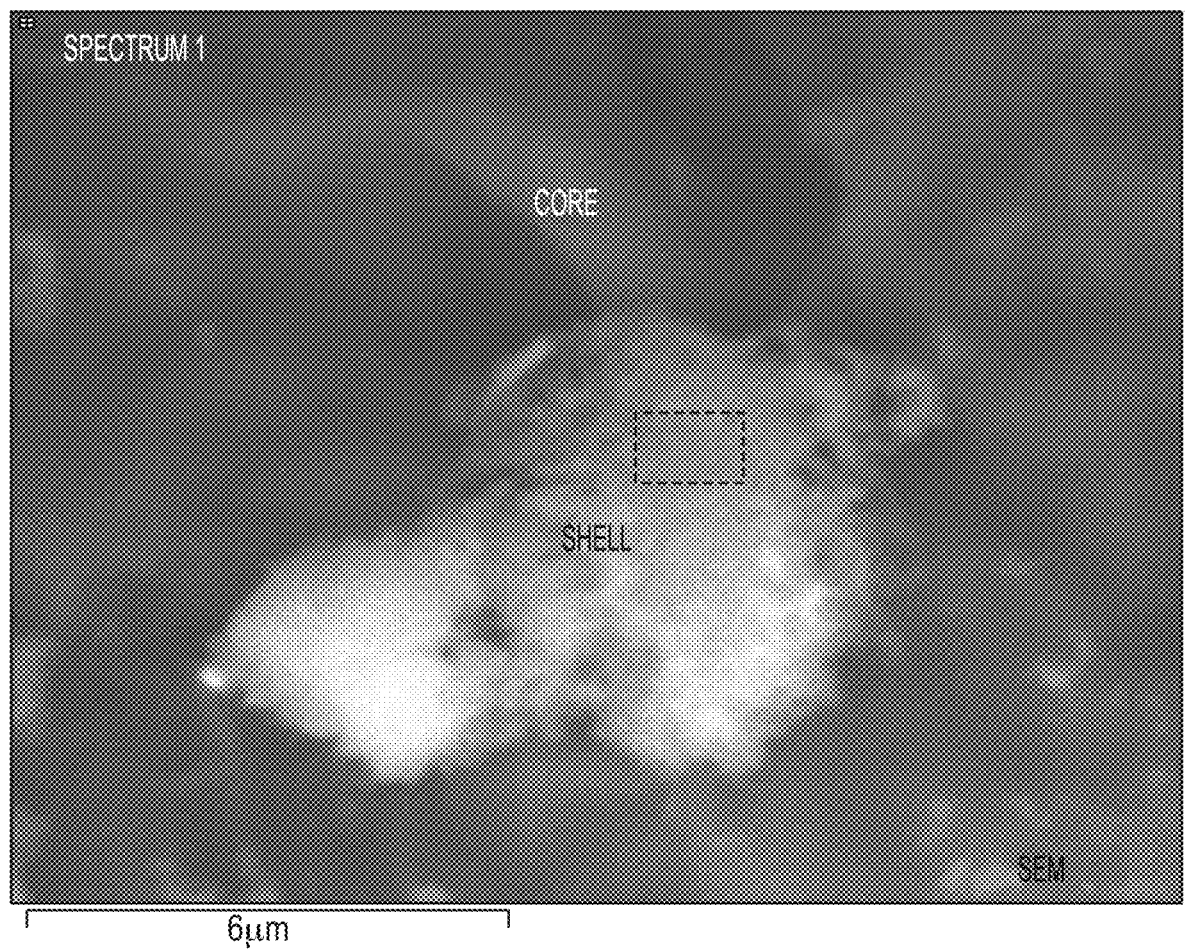
FIG. 10A is an SEM image of still yet another exemplary core-shell MOF composite of the present invention.
Figure 10B:
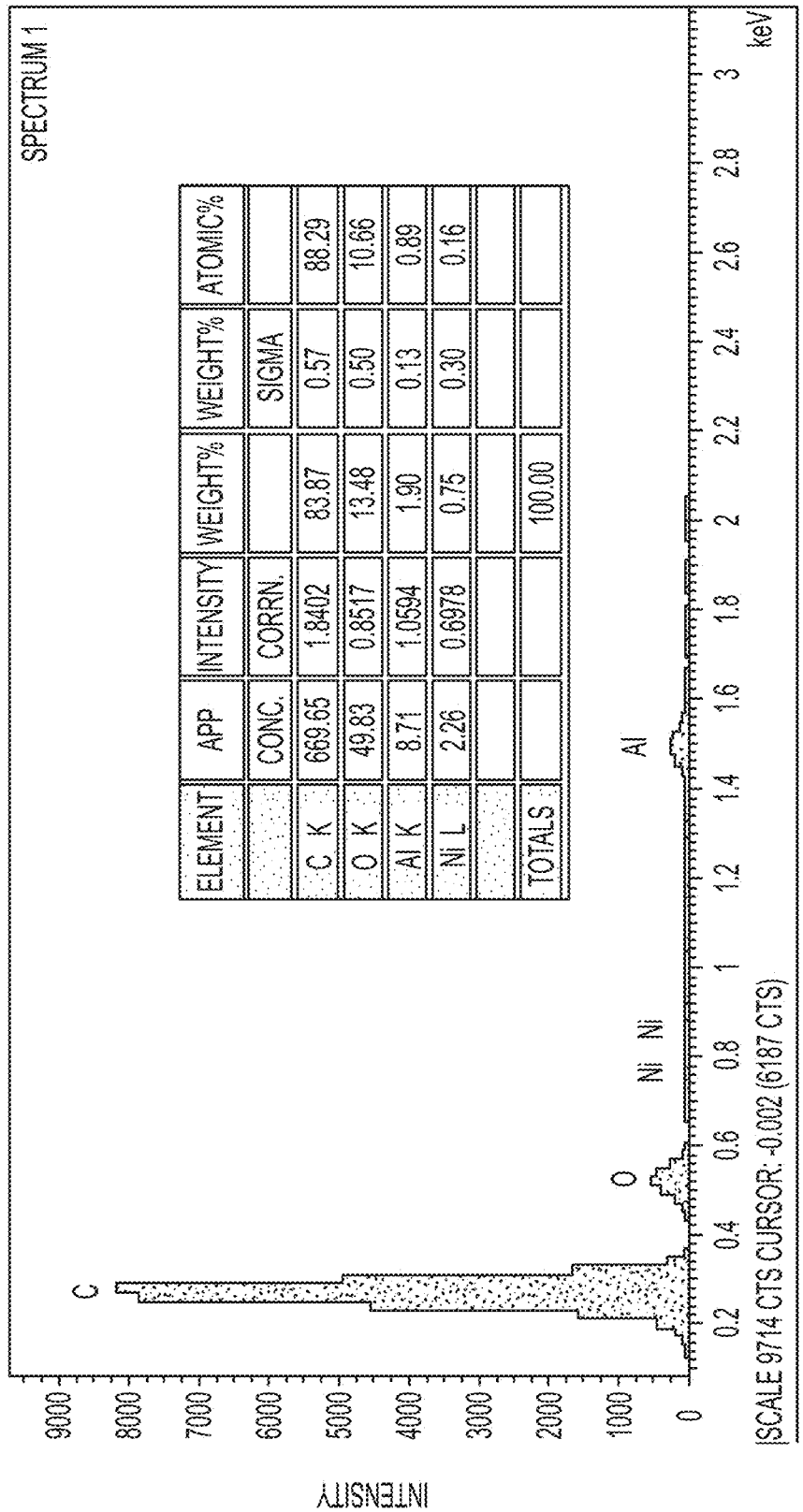
FIG. 10B presents EDX results for the core-shell MOF composite of FIG. 10A.

FIG. 10A presents an SEM image for still yet another exemplary core-shell MOF composite of the present invention. The MOF composite includes a core of an aluminum (Al)-containing MOF (e.g., MIL-53), and a shell of Ni-MOF-74. The SEM image also shows the target location of the probe beam for the EDX analysis described hereafter. FIG. 10B presents data from the EDX analysis of the composite of FIG. 10A. Data show the composite includes both Ni metal in the shell layer of the composite and Al metal in the core of the composite with their respective signal intensities demonstrating the formation of the MOF composite.

Figure 11A:
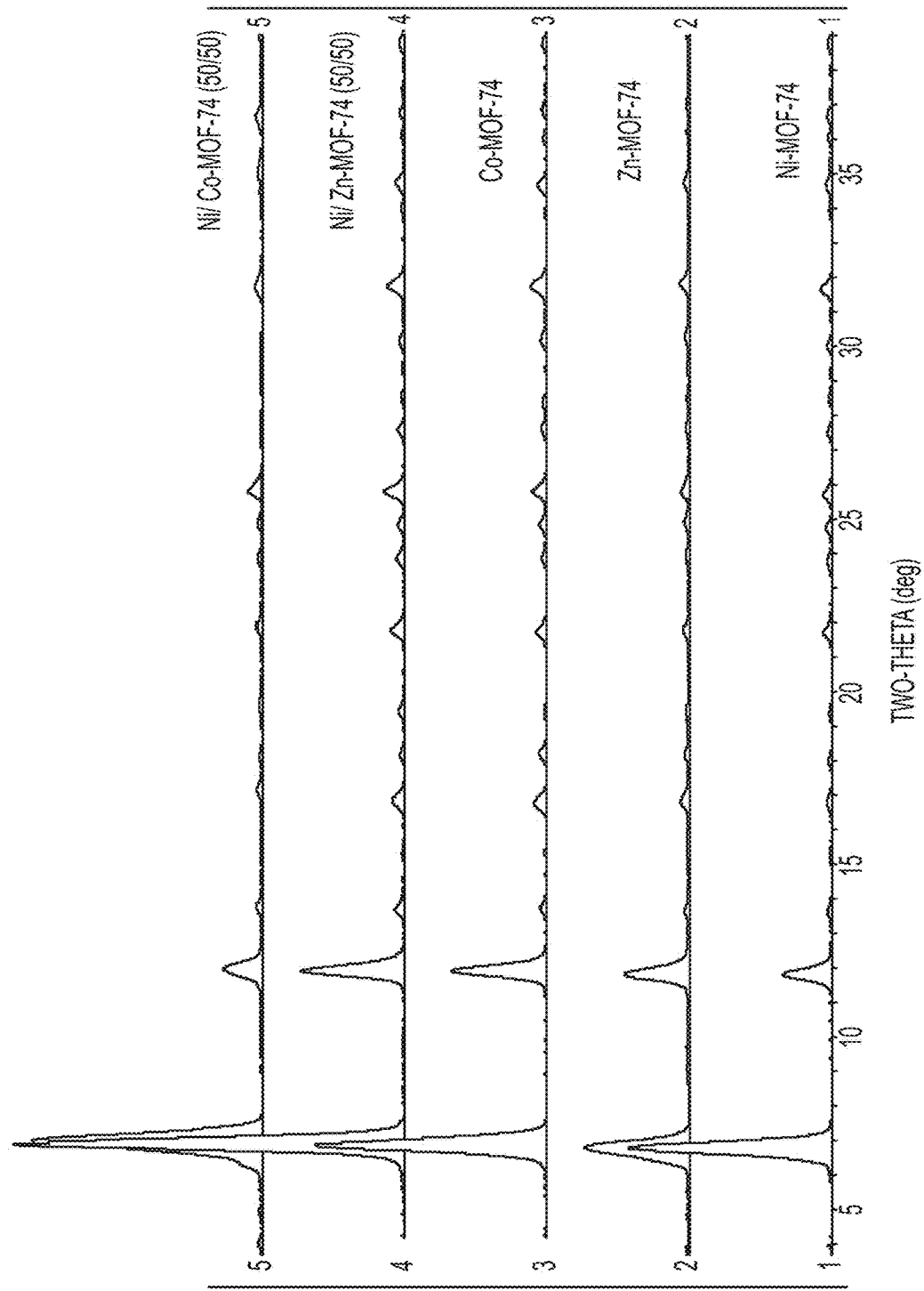
FIG. 11A shows PXRD results for an exemplary mixed-metal MOF composite of the present invention and pure metal MOFs from which the composite is constructed.
Figure 11B:
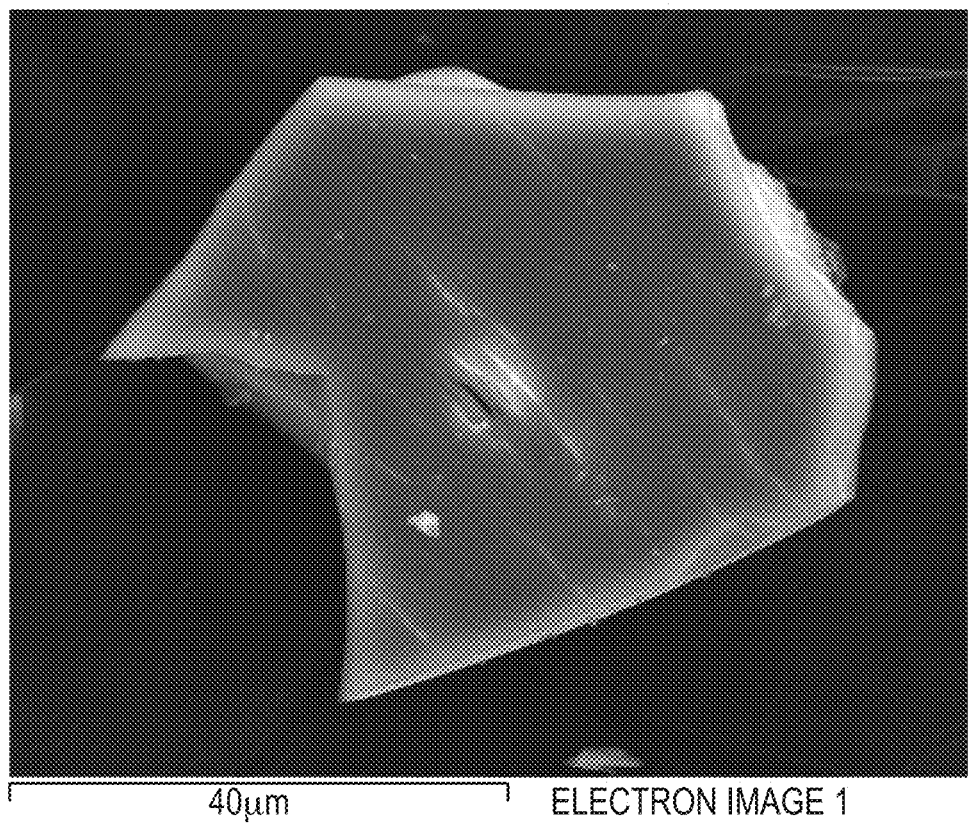
FIG. 11B is an SEM image of the mixed-metal MOF composite of FIG. 11A.

FIG. 11A presents powdered XRD data for exemplary mixed-metal MOF composites of the present invention including a Ni—Zn-MOF-74 composite and a Ni—Co-MOF 74 composite, along with the respective pure metal MOFs from which the composites were synthesized. Data show the mixed-metal MOF structure includes the pure metal MOFs as components, e.g., Ni-MOF-74, Zn-MOF-74, and Co-MOF-74. FIG. 11B shows an SEM image of a mixed-metal composite comprised of a Ni—Zn-MOF-74 MOF and a Ni—Co-MOF-74 MOF described previously in reference to FIG. 11A. FIGS. 11C-11D show electronic mapping images for each of the nickel (Ni) and zinc (Zn) metals in the mixed-metal composite of FIG. 11B. Images show that the Ni and Zn metals are distributed uniformly in the structure including surfaces of the MOF composite. FIG. 11E presents EDX data for the Ni—Zn-MOF-74 mixed-metal composite of FIG. 11B. Data show the presence of both the Ni and Zn metals in the structure of the composite with their respective signal intensities demonstrating the formation of the MOF composite.

Figure 12:
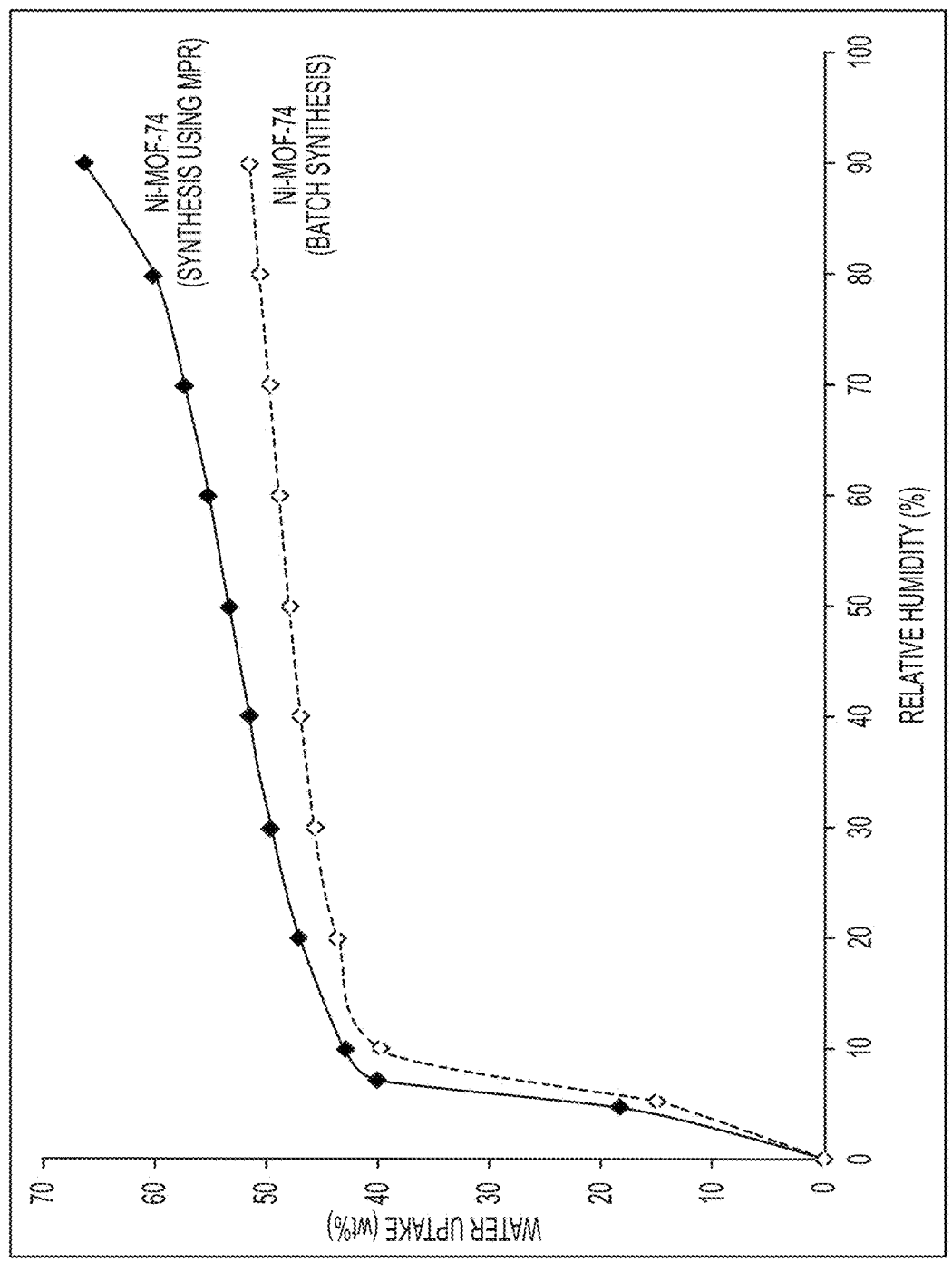
FIG. 12 compares water sorption capacities for an exemplary MOF of the present invention and a MOF synthesized by conventional liquid batch processing.

Properties of MOFs and MOF composites of the present invention were tested. FIG. 12 compares water sorption (uptake) capacities for an exemplary Ni-MOF-74 product synthesized in accordance with the present invention and a MOF made by conventional liquid batch (i.e., solvo-thermal) processing. The MPR-synthesized Ni-MOF-74 product exhibits a superior capacity for adsorption of water at all relative humidity values compared to the batch-synthesized MOF product. Results are attributed at least in part to removal of precursor solvents from pores of nanoscale MOF seed particles immediately upon formation of the particles in the MPR. Unavailability of excess solvent and reactants during formation of the MOF particles yields high purity MOFs in the reactor.

Figure 13:
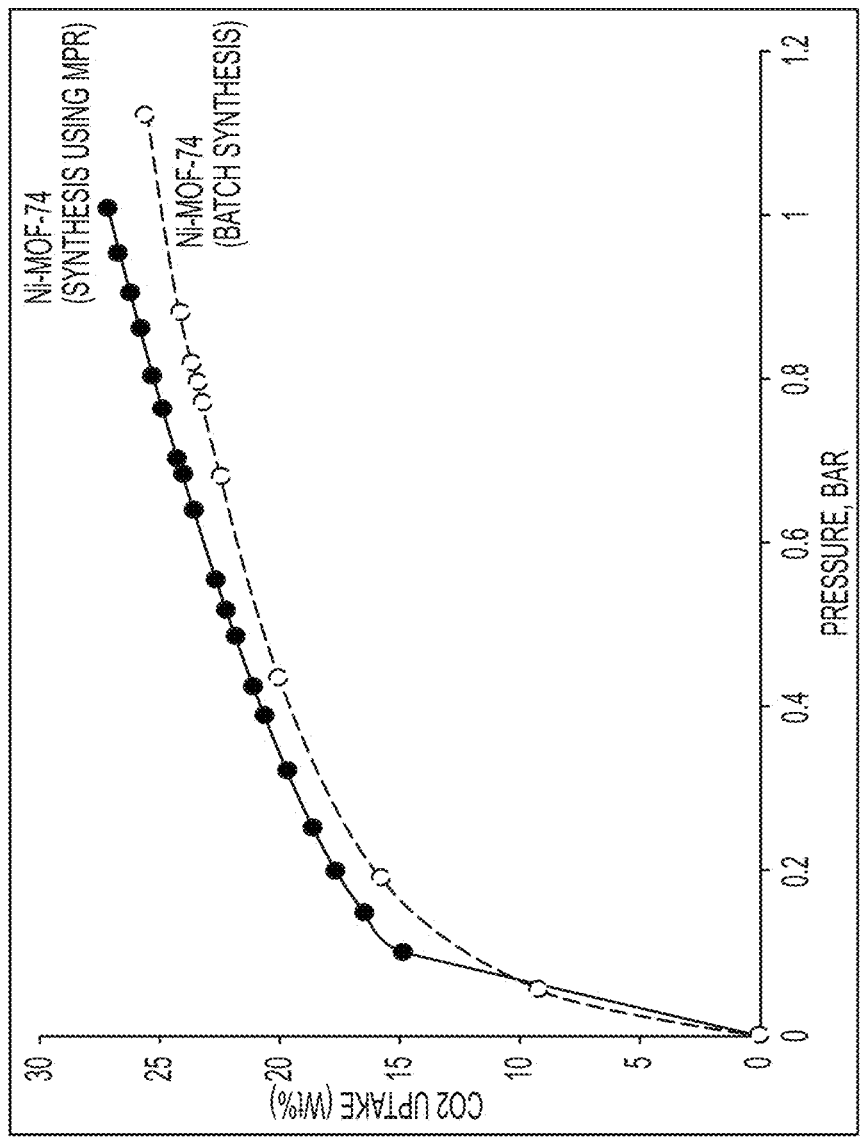
FIG. 13 compares gas sorption capacities for an exemplary MOF of the present invention and a MOF synthesized by conventional liquid batch processing.

FIG. 13 compares $CO_2$ gas sorption capacity for the Ni-MOF-74 product of the present invention and the liquid batch MOF. Results again show the MPR-synthesized Ni-MOF-74 product exhibits a superior capacity for $CO_2$ adsorption at all gas pressures compared to the batch-synthesized MOF product. Other MOFs prepared by the present invention perform similarly. In general, data indicate that MPR-synthesized MOFs and MOF composites exhibit routinely better properties on average than those synthesized by conventional liquid batch processing.

The examples that follow that provide a further understanding of the invention.

Example 1

An exemplary pure MOF, Ni-MOF-74, was synthesized as follows. A MOF precursor solution was prepared by dissolving 30 mmol (e.g., 7.5 g) of a metal precursor containing nickel(II) acetate tetrahydrate in 100 mL water and sonicating for 3 minutes to form a clear solution. A second solution was prepared by mixing 15 mmol (e.g., 3 g) 2,5-dihydroxyterephthalic acid as an organic linker in 100 mL THF solvent and sonicated for 5 min to form a clear solution. The aqueous nickel acetate solution was mixed with THF solution in a [1:1] ratio and sonicated for 3 to 10 minutes to form a clear MOF precursor solution. The MOF production reactor was preheated to a temperature of between about 125° C. to about 150° C. The MOF precursor solution was then introduced into the MPR with a nitrogen carrier gas through a heated inlet at a flow rate of between about 0.05 scfm to 2.0 scfm to form a plume of aerosolized liquid droplets (e.g., of a nanometer size). Pressure in the MPR was less than or equal to about 20 psi during operation. Size of resulting MOF particles was selected by controlling suspension of the MOF particles with the carrier gas and/or recycled solvents in MPR by varying gas flow rates as needed. Resulting MOF particles were separated from the reactor using a cyclone separator. Yield of pure Ni-MOF-74 was greater than 85%. Production quantity was 1 kilogram per day. Greater yields may be obtained with further optimization.

Example 2

Pure metal MOFs including a cobalt metal MOF (Co-MOF-74); a zinc metal MOF (Zn-MOF-74); and a magnesium metal MOF (Mg-MOF-74) were produced using precursor solutions containing selected metal nitrates or metal acetates as the metal source and selected organic linkers listed in TABLE 1. MOF precursor solutions were introduced into MPR at a synthesis temperature of about 150° C.

First run yield of the Co-MOF-74 (unoptimized) was 52%. Other pure MOFs listed in TABLE 1 were prepared using different solvents and molar ratios including, for example, IRMOF-3 at a synthesis temperature of 165° C. [first run yield, ~45% (unoptimized)]; IRMOF-9 at a synthesis temperature of 165° C. [first run yield, 50% (unoptimized)]. Yields greater than 85% were typical. Greater yields may be obtained with further optimization. Other MOFs can be similarly produced including, for example, Mn-MOF-74, Fe-MOF-74, Ti-MOF-74, MOF-5, MOF-177, MOF-180, MOF-200, MOF-210, ZIF-8, TetZB, MOF-801, MOF-841, U10-66, U10-67, U10-68, NU-100, NU-1000, MIL-53, MIL-100, and MIL-101.

Example 3

A MOF precursor solution was prepared by dissolving a metal precursor of copper nitrate nonahydrate (2 mmol) in 100 mL DMF:ethanol:water in a [1:1:1] and sonicated for 3 minutes to form a clear solution. A second solution was prepared by mixing (1 mmol) benzene tricarboxylic acid as an organic linker in 100 mL DMF:ethanol:water in a [1:1:1] ratio and sonicated for 5 min to form a clear solution. Solutions were mixed and sonicated for 3 to 10 minutes to form a clear MOF precursor solution. The MOF production reactor was preheated to a temperature of between about 125° C. to about 160° C. MOF precursor solution was then introduced into the MPR with a nitrogen carrier gas through a heated inlet at a flow rate of between 0.05 scfm to 2.0 scfm to form a plume of aerosolized liquid droplets of a nanometer size. The process was continued until the desired particle size was reached. Size of resulting MOF particles was selected by controlling suspension of the MOF particles in the carrier gas and/or any recycled solvents. Resulting MOF particles were separated from the MPR using a cyclone separator. Yield of pure Cu-MOF-199 (HKUST-1) was ≥80%. Greater yields may be obtained with further optimization.

Example 4

Carbon was sieved to a particle size from about 20 μm to about 50 μm. Typical gravimetric ratios of carbon to MOF of up to 30 wt % (using the expected yield of the MOF product for calculation purposes), with a maximum of up to about 50 wt %, were introduced into the MPR at a temperature of 150° C. (a known maximum yield temperature) and suspended with nitrogen carrier gas flowing at a rate between about 0.5 scfm to about 2.0 scfm. The nickel MOF precursor solution for Ni-MOF-74 was then introduced into MPR. After 30 minutes, flow of MOF precursor solution was stopped and only carrier gas was introduced into MPR for 10 minutes to densify formed MOF particles in the reactor. MOF precursor solution was then again introduced. The process was continued until the desired particle size was reached. Size of resulting MOF composite particles was selected to incorporate the core carbon particles by controlling suspension of the resulting MOF particles in the carrier gas. Particles were separated from the reactor using a cyclone separator. Production quantity was 1 kilogram per day. An unoptimized yield of the core-shell composite was 80%. Greater yields may be obtained with further optimization.

Example 5

A MOF precursor solution was prepared by dissolving 1 mmol (~0.2 g) of nickel silicofluoride ($NiSiF_6$) in 50 mL ethanol and sonicating for 3 minutes to form a clear solution. A second solution was prepared by mixing 2 mmol (~0.16 g) of pyrazine in another 50 mL of ethanol to form a solution. Solutions were mixed and sonicated for 3 to 10 minutes to form a clear MOF precursor solution. MPR was preheated to a temperature of between about 100° C. to about 125° C. MOF precursor solution was then introduced into the MPR with a nitrogen carrier gas to form a plume of aerosolized liquid droplets of a nanometer size. Size of resulting MOF particles were selected by controlling suspension of the MOF particles in the carrier gas and any recycled solvents. Particles were separated from the reactor using a cyclone separator. An alternate pure metal MOF, SIFSIX-3-Co, can be similarly produced.

Example 6

The MPR of FIG. 1 was used. An exemplary mixed metal MOF, Ni—Co-MOF-74, was synthesized as follows. MOF precursor solutions were prepared by dissolving 5 mmol each of a metal precursor nickel(II) acetate tetrahydrate and cobalt acetate tetrahydrate in 100 mL water and sonicating for 3 minutes to form a clear solution. A second solution was prepared by mixing 5 mmol 2,5-dihydroxyterephthalic acid as an organic linker in 100 mL THF solvent and sonicating for 5 min to form a clear solution. Nickel acetate and cobalt acetate solutions were mixed with THF solution in a 1:1 ratio and sonicated for 3 to 10 minutes to form a clear MOF precursor solution. MPR was preheated to a temperature of between about 125° C. to about 150° C. MOF precursor solution was then introduced into the MPR with a nitrogen carrier gas to form a plume of aerosolized liquid droplets of a nanometer size. Unoptimized yield of the Ni—Co-MOF-74 MOF composite was 60%. Yields 85% may be expected with further optimization. Alternate mixed-metal MOFs can be similarly produced including, for example, Ni—Zn-MOF-74 and Co—Zn-MOF-74. No limitations are intended.

Example 7

The MPR of FIG. 1 can be used to synthesize exemplary doped or segmented MOF composites composed of two, three, or more components in accordance with the procedure of EXAMPLE 1 and EXAMPLE 2. In one example, a doped MOF composite can include a first component composed of a quantum dot (QD) material such as a nanoscale particles of semiconducting materials; carbon materials such as carbon nanotubes, carbon nanofibers; graphene oxide; polymers or metal oxides as a second component; and a MOF as a third component. Component concentrations can be varied as needed to achieve the desired amount of doping in the resulting MOF product. In this example, all three components can be introduced simultaneously and continuously into the MPR in separate MOF precursor solutions and aerosolized separately using three different injectors each with a flow of carrier gas into the MPR. Optionally, flows of precursor solutions can be stopped after a selected run time (e.g., 30 minutes) with resulting doped MOFs optionally suspended in the carrier gas for a selected time (e.g., 10 minutes) to densify the particles. Quantities of each component in the MOF composite can be adjusted as needed to form the desired doping in the MOF composite. Flow of carrier gases can also be adjusted to provide suspension of particles in the MPR that achieved selected MOF particle sizes or particle weights. This example is expected to produce a quantity of doped MOF composites of about 1 kilogram per day.

The method and process of the present invention provides continuous aerosolized formation of MOFs and MOF composites that is rapid and controlled. MOFs and MOF composites of the present invention are fully activated immediately following formation so do not need further treatment to remove contaminates. As such, resulting MOFs and MOF composites also have a high purity. Elimination of conventional solvent exchange following synthesis is cost-effective and saves time. The present invention also permits recycling of solvents used in MOF synthesis which reduces MOF production costs by up to 50%. In general, MOFs and MOF composites also exhibit enhanced properties compared to their batch synthesized counterparts. The present invention thus yields scalable quantities and yields of the MOFs and MOF composites and allows new MOF materials to be synthesized that were previously difficult or costly to synthesize.

Applications

MOFs and MOF composites of the present invention find application in gas storage; gas purification; gas and vapor sorption; gas separation; molecular separation; catalysis; heterogeneous catalysis; sensors and sensor applications; adsorption devices; chillers; formation of functional membranes; formation of thin films; production of pharmaceuticals and other specialty materials; and drug delivery. The systems and processes of the present invention allow these MOFs to be reliably, effectively and efficiently created.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

What is claimed is:

1. A continuous method for making Metal Organic Framework (MOF) composites that include a core and a shell about the core, the method comprising:

in one series of steps (1*a*-5*a*), step 1*a*, providing a first MOF solution of a first MOF precursor and a first solvent, wherein the first MOF precursor comprises a salt of a metal selected from the group consisting of cobalt, aluminum and chromium, and a linker selected from the group consisting of a terephthalic acid (MIL-101 or MIL-53), and a dihydoxyterephthalic acid (MOF-74);

step 2*a*, forming a plume of aerosolized liquid droplets of the first MOF solution;

step 3*a*, suspending the aerosolized liquid droplets of the first MOF solution in a carrier gas in a fluidized bed reactor;

step 4*a*, condensing the aerosolized liquid droplets of the first MOF solution to form seed MOF particles;

step 5*a*, removing the first solvent from the MOF seed particles to form cores of the MOF composites;

in another series of steps (1*b*-3*b*), step 1*b*, providing a second MOF solution of a second MOF precursor and a second solvent, wherein the second MOF precursor comprises a Ni-salt and a dihydroxyterephthalic acid (MOF-74);

step 2*b*, forming a plume of aerosolized liquid droplets of the second MOF solution;

step 3*b*, suspending the aerosolized liquid droplets of the second MOF solution in the carrier gas in the fluidized bed reactor;

and further, condensing the aerosolized liquid droplets of the second MOF solution of the step 3*b* to form the shell onto the existing MOF cores of the step 5*a* to form the MOF composites;

removing the second solvent from the MOF composites, wherein the MOF composites are from 200 um to 1500 um in size.

2. The method of claim 1 further comprising recovering the first and the second solvents from the reactor and recycling the solvents to form the first and the second MOF solutions comprising the first and the second MOF precursors.

3. The method of claim 1 wherein the aerosolizing the first and the second MOF solutions to form the aerosolized liquid droplets comprises ultrasonically aerosolizing the solutions.

4. The method of claim 1 further comprising providing the MOF composites to a separation device configured to separate the composites by size.

5. The method of claim 1 wherein the MOF composites comprise one or more of: Ni-MOF-74(shell)/Cr-MIL-101 (core); Ni-MOF-74(shell)/Co-MOF-74(core); or Ni-MOF-74(shell)/Al-MIL-53(core).

* * * * *

UNITED STATES PATENT AND TRADEMARK OFFICE
CERTIFICATE OF CORRECTION

PATENT NO. : 10,695,741 B2
APPLICATION NO. : 15/186004
DATED : June 30, 2020
INVENTOR(S) : Radha Kishan Motkuri, Jagannadha R. Bontha and B. Peter McGrail Page 1 of 1

It is certified that error appears in the above-identified patent and that said Letters Patent is hereby corrected as shown below:

On the Title Page

(56) References Cited, 2nd Column, 19th Line – Replace "AU 2015293627 B1 12/2015" with
--AU 2015203627 B1 12/2015--

(56) References Cited FOREIGN PATENT DOCUMENTS, 2nd Column, 20th-21st Lines – Remove
"WO WO PCT/US2017/026242 7/2017"

(56) References Cited FOREIGN PATENT DOCUMENTS, 2nd Column, 22rd-23rd Lines – Remove
"WO WO PCT/US2017/026242 12/2018"

(56) References Cited OTHER PUBLICATIONS, page 2, 1st Column, 22nd Line – Add
--WO PCT/US2017/026242 Search Rept. dated July 14, 2017, Battelle Memorial Institute.
WO PCT/US2017/026242 Writ. Opin. dated July 14, 2017, Battelle Memorial Institute.--

(56) References Cited OTHER PUBLICATIONS, page 2, 1st Column, 26th Line – Add
--WO PCT/US2017/026242 IPRP dated Dec. 18, 2018, Battelle Memorial Institute.--

In the Specification

Column 16, Line 27 – Replace "that follow that provide a further" with --that follow provide a
further--

Signed and Sealed this
Eleventh Day of January, 2022

Drew Hirshfeld
*Performing the Functions and Duties of the
Under Secretary of Commerce for Intellectual Property and
Director of the United States Patent and Trademark Office*